«12» United States Patent
Ray et al.

US007232893B2

(10) Patent No.: US 7,232,893 B2
(45) Date of Patent: Jun. 19, 2007

(54) METHOD OF MANUFACTURING A STELLATE CELL DEATH FACTOR

(75) Inventors: Ranjit Ray, Saint Louis, MO (US); Ratna Ray, Saint Louis, MO (US); Arnab Basu, Kolkata (IN); Yie-Hwa Chang, Saint Louis, MO (US)

(73) Assignee: Saint Louis University, St. Louis, MO (US)

( * ) Notice: Subject to any disclaimer, the term of this patent is extended or adjusted under 35 U.S.C. 154(b) by 199 days.

(21) Appl. No.: 10/888,962

(22) Filed: Jul. 9, 2004

(65) Prior Publication Data

US 2005/0266531 A1  Dec. 1, 2005

Related U.S. Application Data

(60) Provisional application No. 60/487,126, filed on Jul. 12, 2003.

(51) Int. Cl.
*C07K 1/18* (2006.01)
*C12N 5/00* (2006.01)

(52) U.S. Cl. ............... 530/416; 435/70.1; 435/405; 530/300; 530/350

(58) Field of Classification Search ............ None
See application file for complete search history.

(56) References Cited

U.S. PATENT DOCUMENTS

| 5,869,243 | A | * | 2/1999 | Jauregui et al. ........... 435/6 |
| 5,994,298 | A | | 11/1999 | Tsai et al. |
| 6,258,779 | B1 | | 7/2001 | Tsai et al. |
| 2001/0049356 | A1 | | 12/2001 | Tsai |
| 2003/0027767 | A1 | | 2/2003 | Tsai |
| 2003/0087809 | A1 | | 5/2003 | Tsai |

OTHER PUBLICATIONS

Basu et al. Stellate cell apoptosis by a soluble mediator from immortalized human hepatocytes. Apoptosis 11: 1391-1400, 2006.*
Schippers et al. Immortalized human hepatocytes as a tool for the study of hepatocytic (de-)differentiation. Cell Biol Toxicol 13: 375-386, 1997.*
Basu et al., "Hepatitis C Virus Core Protein Is Necessary for the Maintenance of Immortalized Human Hepatocytes," Virology 298:53-62 (2002).
Basu et al., "Primary Human hepatocytes immortalized by . . . ," 22nd Annual Meeting, American Society For Virology, Jul. 12-16, 2003, Advise, USA.
Buck et al., "C/EBPbeta Phosphorylation by RSK Creates a Functional XEXD Caspase . . . ," Molecular Cell 8:807-816 (Oct. 2001).
Yu and Tsai., "Fetal fetuin selectively induces apoptosis . . . ," Cancer Letters 166:173-184, May 26, 2001 (abstract).
Dziegielewska et al., "The Complete cDNA and Amino Acid Sequence of Bovine Fetuin," J. Biol. Chem. 265:4354-4357 (Mar. 15, 1990).
Forestier et al., "Application of mRNA differential display to liver cirrhosis . . . ," Biochem. Biophys. Res. Commun. 225:377-383, Aug. 14, 1996 (abstract).
"Hepatic Fibrosis— Role of Hepatic Stellate Cell Activation part 5 of 6," HBV Research Archives, 3 pages, Jul. 25, 2002.
ISSA et al., "Apoptosis of hepatic stellate cells: involvement in resolution of biliary fibrosis and regulation by . . . ," Gut 48:548-557, 2001.
ISSA et al., "Mutation in collagen-1 that confers resistance to the action of collegenase results in . . . ," The FASEB Journal 17:47-49, Jan. 2003.
Jahnen-Dechent et al., "Posttranslational processing of human alpha 2-HS glycoprotein . . . ," Eur. J. Biochem. 226:59-69, Nov. 15, 1994 (abstract).
Ohnishi et al., "Effects of Cytokines and Growth Factors on Phosphorylated Fetuin Biosynthesis . . . ," Biochem. Biophys. Res. Comm. 200:598-605, Apr. 15, 1994 (abstract).
Ohnishi et al., "Effect of Phosphorylated Rat Fetuin on the Growth of Hepatocytes in Primary Culture . . . ," Eur. J. Biochem. 243:753-761, Feb. 1, 1997 (abstract).
Ray et al., "Hepatitis C Virus Core Protein Promotes Immortalization of Primary Human Hepatocytes," Virology 271:197-204, 2000.
Yao et al., "Effects of Yigan Decoction on proliferation and apoptosis of hepatic stellate cells," World J. Gastroenterol. 8:511-514, Jun. 15, 2002.
Zhang et al., "Salvia miltiorrhiza monomer IH764-3 induces hepatic stellate cell apoptosis via caspase-3 activation," World J. Gastroenterol. 8:515-519. Jun. 15, 2002.

* cited by examiner

*Primary Examiner*—Bridget Bunner
(74) *Attorney, Agent, or Firm*—Joseph E. Zahner

(57) ABSTRACT

The present invention provides compositions and methods for selectively inhibiting the proliferation of stellate cells, which are important for the development of liver fibrosis upon liver injury. The invention describes conditioned media from immortalized hepatocytes as containing a death factor that induces apoptosis of activated liver stellate cells. This pro-apoptotic activity is shown to be associated with an 80 kDa protein, which is associated with a fetuin peptide sequence and an albumin peptide sequence.

5 Claims, 10 Drawing Sheets

A

Hepatocytes　　　Stellate Cells

B

C

A   B

A

B

METHOD OF MANUFACTURING A STELLATE CELL DEATH FACTOR

PARENT CASE TEXT

This application claims benefit of priority to U.S. Provisional Patent Application No. 60/487,126, filed Jul. 12, 2003.

SEQUENCE LISTING

A paper copy of the sequence listing and a computer readable form of the same sequence listing are appended below and herein incorporated by reference.

BACKGROUND OF THE INVENTION

1. Field of the Invention

This invention relates generally to compositions and methods of treating liver fibrosis or cirrhosis. Specifically, the invention is directed to compositions and methods for killing liver stellate cells.

2. Description of the Related Art

According to the American Liver Foundation, over 300,000 Americans are hospitalized each year for cirrhosis of the liver. The primary causes of cirrhosis are alcohol abuse and chronic hepatitis C. To date, approximately 3.9 million Americans suffer from Hepatits C. It is also estimated that 18,000 people are in need of liver transplants, which are in woefully short supply. Thus, it is essential to saving lives that new medical treatments for preventing and reversing liver cirrhosis are developed.

Hepatitis C virus (HCV) is a major causative agent of acute and chronic hepatitis, which may lead to liver cirrhosis and hepatocellular carcinoma (Choo, Q. L. et al, 1989; Di Bisceglie, A. M. 1997; Saito I. et al 1990). Natural immune responses are not capable of terminating HCV infection in most patients. Furthermore, neither a vaccine nor any other means of very effective therapy is available to control HCV (McHutchison et al., 1998). Immune evasion and a quasispecies nature are prominent features of HCV (Farci et al., 1992; Weiner et al., 1992; Purcell, 1994). The molecular mechanisms whereby HCV circumvents the immune response, persists, and causes chronic liver disease is not well understood. However, these processes would likely require immune mediated factors, and the interaction of viral proteins with cellular factors (Rehermann and Chisari, 2000).

HCV contains a single positive-stranded RNA as its genome. HCV genome encodes a precursor polypeptide of ~3,000 amino acids. This precursor polypeptide is cleaved by both host and viral proteases to at least 10 individual proteins: C, E1, E2, p7, NS2, NS3, NS4A, NS4B, NS5A, and NS5B (Clarke, B. 1997). Diverse functional activities of the HCV core protein have already been noted by a number of investigators (Ray and Ray, 2001-FEMS). Our own work and the results from other laboratories suggest that the core protein has multifunctional activities. These include encapsidation of viral RNA, a regulatory effect on cellular and unrelated viral promoters, interactions with a number of cellular proteins, a modulatory role in programmed cell death or apoptosis under certain conditions, involvement in cell growth promotion and immortalization, induction of HCC in transgenic mice, and a possible immunoregulatory role. These intriguing properties suggest that the core protein, in concert with diverse cellular factors, may contribute to pathogenesis during persistent HCV infection.

Hepatic stellate cells (HSC) constitute approximately 15% of the total number of resident liver cells, and are the pivotal cell type involved in the development of hepatic fibrosis (McGee J O, J Pathol; 106, 1972; McGee J O, Lab Invest; 26:429-440, 1972). Following liver injury of any etiology, HSC are activated from quiescent cells into proliferative, fibrogenic, and contractile myofibroblasts (Friedman, 2000, and Proc Natl Acad Sci USA 1985; 82: 8681-8685. and Rockey D C, Submicrosc Cytol Pathol 1992; 24:193-203.). The survival of activated HSC in liver injury is dependent on soluble growth factors and cytokines, and on components of the fibrotic matrix (Iredale, 2001).

Liver fibrosis is a central feature of the majority of chronic liver injuries due to metabolic, genetic, viral, and cholestatic diseases. It results in distortion of the liver architecture (cirrhosis), which is associated with disturbance of liver function and significant morbidity and mortality (Friedman S L. N Engl J. Med., 328:1828-1835, 1993). During the liver injury these cells are activated and the process involves cell proliferation and acquisition of fibrogenic and contractile capacity. Liver hepatocytes plays an important role in this activation (Smith et al; 2003; Hepatology). The resolution of hepatic fibrosis is associated with the remodeling of the excess liver matrix and may result in restitution of near normal liver architecture in patients (J. F. Dufour, et al Dig Dis Sci. 1998, 43 2573-2576; J. F. Dufour, et al. Ann Intern Me, 199,7 127, 981-98; Kaplan, R. A. et al. Ann Intern Med. 1997, 126, 682-688) and experimental animal models (G. Abdel-Aziz, 1990). An essential element of this recovery process is the apoptosis of activated HSC (J. P. Iredale et al J Clin Invest. 1998, 102 538-549). Understanding the mechanisms of HSC apoptosis might provide insight into novel therapeutic approaches to treat advanced hepatic fibrosis. HSC apoptosis are shown to be induced by activated Kupffer cells through a novel mechanism (Fischer R, et al. Gastroenterology. 2002; 123:845-61) and by ligands of the peripheral type benzodiazepine receptor (Fischer R, et al. Gastroenterology. 2001; 120:1212-1226). However, very little is known about the role of hepatocytes for HSC apoptosis. Murine hepatocytes have been shown to secreate an inducing protein that selectively causes apoptosis in liver (Ikeda et al, Immunology, 2003, 108,116-122). Hepatic stellate cells, when isolated and grown on plastic surface, spontaneously undergo activation. This culture induced activated stellate cells have been extensively studied as a model cell line of liver fibrogenesis.

The inventors have sought to address the issue of liver homeostasis and disease, particularly the interaction between hepatocytes and stellate cells. Is stellate cell growth controlled by immortalized hepatocytes? Do activated stellate cells in turn regulate hepatocyte growth? Understanding these interactions will offer new avenues for therapeutic strategies to combat liver disease.

SUMMARY OF THE INVENTION

The inventors have made the surprising discovery that conditioned medium from immortalized hepatocytes ("immortalized hepatocyte-conditioned medium") contains a death factor, which comprises a biochemical activity, which is the promotion of apoptosis of a liver stellate cell ("pro-apoptotic activity"). The inventors have demonstrated that the pro-apoptotic activity is inactivated by (a) heat treatment, wherein the pro-apoptotic activity can be inactivated at 56° C. for 5 minutes, (b) treatment with albumin or (c) treatment with protease inhibitors that are not metalloprotease inhibitors. The inventors have demonstrated that the pro-apoptotic activity is not affected by treatment with (a) metallo-protease inhibitors or (b) antibodies to known pro-apoptotic factors, such as TRAIL and Fas ligand.

Furthermore, the pro-apoptotic activity has been purified from immortalized hepatocyte-conditioned medium following a standard column chromatography protocol (FIG. 4; infra). The pro-apoptotic activity has been found to co-purify with a major polypeptide of approximately 80 kD (FIG. 10) and a minor polypeptide of approximately 120 kD (FIG. 10), as determined by reducing SDS polyacrylamide gel electrophoresis. N-terminal microsequencing of this associated protein revealed the following sequences: DTH-KSEIA (SEQ ID NO:9), which corresponds to bovine albumin, and IPLDPVAGYK (SEQ ID NO:1), which corresponds to bovine fetuin (a.k.a. bovine α-2HS glycoprotein). However, the inventors have herein demonstrated that (a) inactivating antibodies to human α-2HS-glycoprotein fail to inhibit the pro-apoptotic activity associated with 80 kD protein; (b) anti-BSA antibodies pull down the 80 kD protein and concomitant pro-apoptotic activity.

Therefore, an object of this invention is a method of inhibiting the proliferation of stellate cells, by inducing apoptosis in stellate cells, by contacting the stellate cells with a death factor. The death factor may be in media, such as immortalized hepatocyte conditioned media, or media conditioned by other immortal hepatocytes or hepatoma cells. The death factor may be purified, such as according to an ion exchange process, and the purified composition, which comprises an approximately 80 kD protein, a pro-apoptotic activity, a fetuin (a.k.a. α-2HS glycoprotein) sequence and an albumin sequence, may be administered to stellate cells to induce apoptosis.

In another embodiment, the invention is directed to a stellate cell death factor, which is purified, either partially, fully, or as part of a complex of proteins including fetuin, albumin, a 80 kDa protein, a 120 kDa protein, or a combination of any two or more of said proteins, from media conditioned by immortalized hepatocytes or hepatoma cells ("conditioned media" or "CM"). It is envisioned that a fragment or fragments of fetuin, the 80 kD or 120 kD protein may have pro-apoptotic activity toward stellate cells. It is also envisioned that a pro-apoptotic activity toward stellate cells may be imbued in a separate factor or factors that are not directly fetuin, fetuin fragments, modifications of fetuin or the 80 kD or 120 kD protein, but are rather bound to fetuin as part of a ternary complex that purifies together according to the three step ion exchange procedure (summarized in FIG. 4). It is also envisioned that the pro-apoptotic activity resides in a binary or ternary complex comprising the 120 kDa protein, 80 kD protein, albumin or fetuin. In a preferred embodiment, the inventor envisions that the stellate cell death factor comprises an approximately 80 kD heat labile protein that is capable of binding to albumin, α-2HS glycoprotein, or both.

In yet another embodiment, the invention is drawn to a method of manufacturing a stellate cell death factor, comprising the steps of (a) conditioning media with an immortalized hepatocyte or hepatoma cell to produce conditioned media ("CM") which comprises the stellate cell death factor, and then optionally (b) applying the CM to an anion exchange column, (c) applying the resultant flow-through to a first cation exchange column, (d) eluting a fraction comprising the stellate cell death factor with 0.5 M NaCl, (e) dialyzing eluant into a first buffer, (f) applying dialysate onto a second cation exchange column, (g) and eluting fractions comprising the stellate cell death factor using a 50 to 500 nM NaCl gradient.

It is envisioned that the instant stellate cell death factor (supra) may be administered to stellate cells in vivo, in a pharmaceutically acceptable formulation, as a therapy for the treatment of a hepatic fibrosis disease or liver cirrhosis.

DETAILED DESCRIPTION OF THE INVENTION

Figure 1:
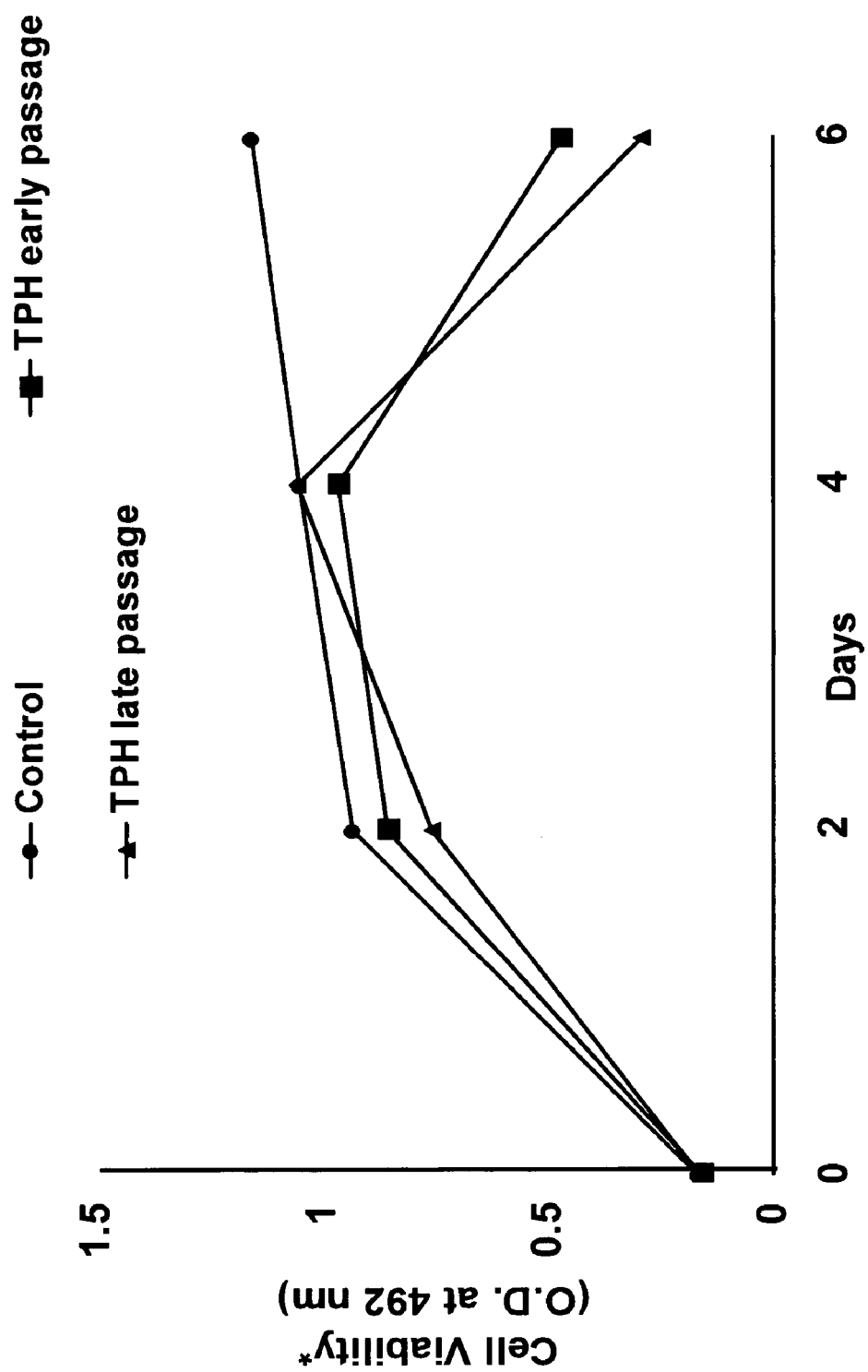
FIG. 1: Growth of human stellate cells in conditioned medium from immortalized hepatocytes (TPH-1, passage 10 or passage 50) and medium from THLE as a negative control. The growth was measured using a Cell Titer TM AQueous Non-Radioactive Cell Proliferation Assay (Promega).

The inventors have shown previously that hepatitis C virus (HCV) core protein immortalizes primary human hepatocytes. A role of the immortalized hepatocytes (IH) on mammalian (e.g., human and rat) hepatic stellate cell growth regulation is herein disclosed. Preferential growth of IH was observed when cocultured with activated mammalian liver stellate cells. Further studies disclosed herein suggest that mammalian stellate cells undergo apoptosis when grown together with IH in a dual chamber or when incubated with conditioned medium from IH. However, mammalian liver stellate cell death was not observed when incubated with conditioned medium from non-hepatic neoplastic cell lines or from an epithelial cell line, indicating that IH generate soluble mediator(s) for stellate cell cytotoxicity. The effect of hepatocyte conditioned media on stellate cells was not due to FasL, TGF-β, TRAIL, IL-7 or IL-8, as neutralizing antibodies to these cytokines/growth factors did not prevent cell death. Subsequent analysis suggested that treatment of mammalian liver stellate cells with conditioned medium from IH increases TRAIL receptors (e.g., DR4 and DR5), and apoptosis was found to be associated with the activation of several caspases and the cleavage of PARP. Stellate cell death factor released by IH in conditioned medium was found to be heat labile. The soluble modulator was purified by biochemical and analytical procedures and copurified with a protein having a molecular weight of ~80 kD (kD=$10^3$ Daltons). Together, these observations suggest that the control of activated stellate cell growth by immortalized hepatocytes may have important implications in cirrhosis and hepatocellular carcinoma.

Therefore, the invention is drawn to (1) a stellate cell death factor comprising a pro-apoptotic activity, which may be contained in or derived from immortalized hepatocyte conditioned media or associated with an 80 kD protein or a fetuin polypeptide, (2) methods of killing stellate cells by apoptosis by administering to stellate cells the stellate cell death factor, and (3) methods of manufacturing a liver stellate cell death factor. The stellate cell may be ex vivo or in a patient who suffers from a hepatic fibrosis disease, of which cirrhosis of the liver is an example.

The term "death factor" means any agent that promotes the killing of any cell. Killing may be by necrosis or apoptosis (programmed cell death). A "stellate cell death factor" promotes the preferential killing of liver stellate cells relative to hepatocytes. A death factor may be a metal, enzyme or other polypeptide, protein, ternary complex of biological molecules, peptide fragment, nucleic acid or polynucleotide, lipid, fatty acid, carbohydrate, secondary messenger molecule, ion, atom, or compound.

The term "pro-apoptotic activity" means the act of, or the capability of, promoting or inducing apoptosis (a.k.a. programmed cell death), which is characterized by cellular blebbing and DNA laddering. Pro-apoptotic activity may reside inherently in a biological molecule, such as a polypeptide, or a ternary complex comprising a polypeptide. Pro-apoptotic activity may reside inherently with the instant 80 kD protein or a fetuin polypeptide or fragment thereof.

The term "fetuin" is equivalent to "alpha-2-HS glycoprotein" and means a polypeptide belonging to the fetuin family of proteins. Table 1 provides the GenBank accession numbers of exemplary fetuin polypeptides, as well as a summary of the sequence identities between the mammalian fetuin (a.k.a. alpha-2-HS glycoprotein). A preferred fetuin or alpha-2-HS glycoprotein comprises a sequence that is at least 60% identical to the human alpha-2-HS glycoprotein sequence as set forth in SEQ ID NO:6.

Sequence identity or percent identity is intended to mean the percentage of same residues between two sequences. The reference sequence is human alpha-2-HS glycoprotein (human fetuin). In all of the sequence comparisons, the two sequences being compared are aligned using the Clustal method (Higgins et al, Cabios 8:189-191, 1992) of multiple sequence alignment in the Lasergene biocomputing software (DNASTAR, INC, Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in Atlas of Protein Sequence and Structure, Dayhoff, Ed., NBRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Using this criterion, preferred conservative amino acid changes are: R-K; E-D, Y-F, L-M; V-I, Q-H. Conservation is referenced to human alpha-2-HS glycoprotein when determining percent conservation with alpha-2-HS glycoprotein from other species.

Table 1 shows the calculations of identity for comparisons of alpha-2-HS glycoprotein (a.k.a. fetuin) from various species relative to human α-2HS glycoprotein.

TABLE 1

Percent Identity of alpha-2-HS-glycoprotein sequences

| Species | Accession Number | Percent Identity |
|---|---|---|
| Human | NP 001613 | 100 |
| Bovine | NP 776409 | 64 |
| Mouse | AAH1988 | 60 |
| Rat | NP 037030 | 61 |

The term "immortalized hepatocyte" means any cell that is capable of secreting albumin or alpha-2-HS glycoprotein, and can survive in culture for at least 5 weeks. Non-limiting examples of immortalized hepatocytes include transfected primary human hepatocytes ("TPH cells"), which are primary hepatocytes that have been transformed with a DNA encoding all or part of a hepatitis C viral core protein, and immortal hepatocytes, hepatomas or hepatocarcinoma cells. A preferred immortalized hepatocyte expresses telomerase.

The term "immortalized hepatocyte conditioned media" means any tissue culture medium in which immortalized hepatocytes have been grown for any period of time. A preferred immortalized hepatocyte medium contains a stellate cell death factor.

The term "inhibiting proliferation" means inhibiting the growth or division of a cell, inhibiting the transit by a cell through the cell cycle, preventing a cell from exiting G0 of the cell cycle, inducing a cell to become quiescent, killing a cell, promoting the death of a cell, inducing apoptosis of a cell, reducing the rate of an increase in cell number in a population of cells, or decreasing the number of cells in a population.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Immortalized Hepatocytes Induce Stellate Cell Apoptosis

We have previously shown that hepatitis C virus (HCV) core protein immortalizes primary human hepatocytes (Ray et al., 2000; Basu et al., 2002). In this study, we investigated the role of the immortalized hepatocytes (TPH) on regulation of hepatic stellate cell growth. Preferential growth of the immortalized hepatocytes was observed when co-cultured with an activated hepatic stellate cell (LX2) line. Further studies suggested that LX2 cells undergo apoptosis when grown with TPH cells in dual chambers or incubated with conditioned medium from TPH cells. However, LX2 cell death was not observed when incubated with conditioned media from a number of nonhepatic epithelial cells (HeLa, BHK, or MCF-7), indicating that TPH cells secrete a specific death factor. The effect of the conditioned media from TPH on LX-2 cells was not due to FasL, TGF-beta, TRAIL, IL-7 or IL-8, as neutralizing antibodies to these cytokines growth factors did not prevent LX2 cell death. LX2 cell death factor released by immortalized TPH was enriched and purified by employing biochemical and analytical separation procedures. The secretory death factor was found to be heat labile, and has a molecular weight of ~80 kD. The inhibitory role of TPH on hepatic stellate cells may have an important implication in HCV mediated liver disease progression.

Immortalized human stellate cells LX-2 (kindly provided by Scott Friedman, Moun Sinai School of Medicine, NY), when cultured on matrigel coated plates in SABM (Clonetics, Calif.) supplemented with glutamine (2× concentration) and 0.2% BSA, formed extensive network like structure. LX-2 cells growing on matrigel, when incubated with used culture medium (conditioned medium-CM) from TPH or THLE (primary human hepatocytes immortalized by SV 40 T antigen-kindly provided by Curtiss C. Harris, NCI) stably transfected with HCV core gene, became granular and cell death occurred within 6 days. However, cell death was not observed when LX2 cells were incubated with CM from THLE as a negative control.

Figure 2:
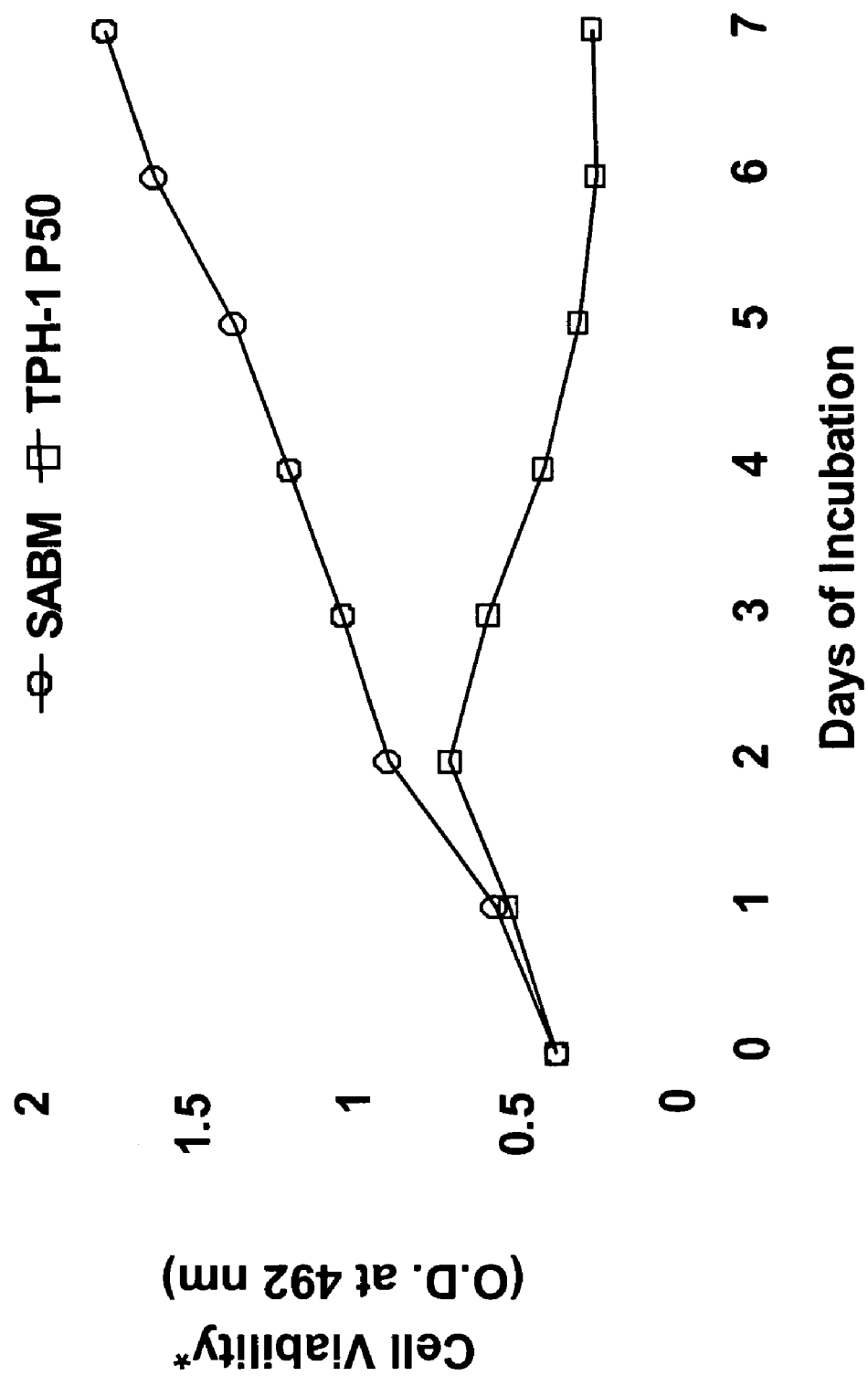
FIG. 2: Growth of rat stellate cells in conditioned medium from immortalized hepatocytes (TPH-1, passage 50) and medium from SABM as a negative control. The growth was measured using a Cell Titer TM AQueous Non-Radioactive Cell Proliferation Assay (Promega).

LX2 cells plated on a plastic surface grew as activated stellate cells. Upon incubation with CM from TPH or THLE-core, LX-2 cells became granular after three days and cell death was observed (FIG. 1). However, LX-2 cells incubated with CM from THLE or HepG2 cells grew relatively faster as compared to cells grown in normal media. We also examined the role of CM from human hepatocytes on rat stellate cells. Primary rat stellate cells (kindly provided by Bruce Bacon, Division of Gastroenterology, Saint Louis University) growing on matrigel coated plate displayed cell death upon incubation with CM from TPH or THLE-core (FIG. 2). On the other hand, CM from THLE (negative control) displayed slightly higher cell growth. These preliminary results suggested that conditioned medium from HCV core transfected hepatocytes causes both human and rat stellate cell death.

Immortalized hepatocytes (TPH) displayed preferential growth when cocultured with activated hepatic stellate (LX2) cells. Further studies suggested that LX2 cells die when grown with TPH in dual chambers or incubated with conditioned medium from TPH even at a 1:64 dilution. However, LX2 cell death was not observed when incubated with conditioned media from hepatocytes or from nonhepatic epithelial cells (HeLa, BHK, or MCF-7), indicating that TPH secrete a specific death factor for LX2 cells. Interestingly, the secretory death factor was found to be heat labile when treated at 56° C. for 5 min. LX2 death factor(s) released by TPH was enriched by ultrafiltration for molecular size cut-off and by ion-exchange chromatography (infra). The active factor responsible for HSC appeared to have a molecular weight between 80-100 kD. Stellate cell cytotoxicity by conditioned medium from TPH may have important implication in HCV mediated liver disease progression.

Figure 3:
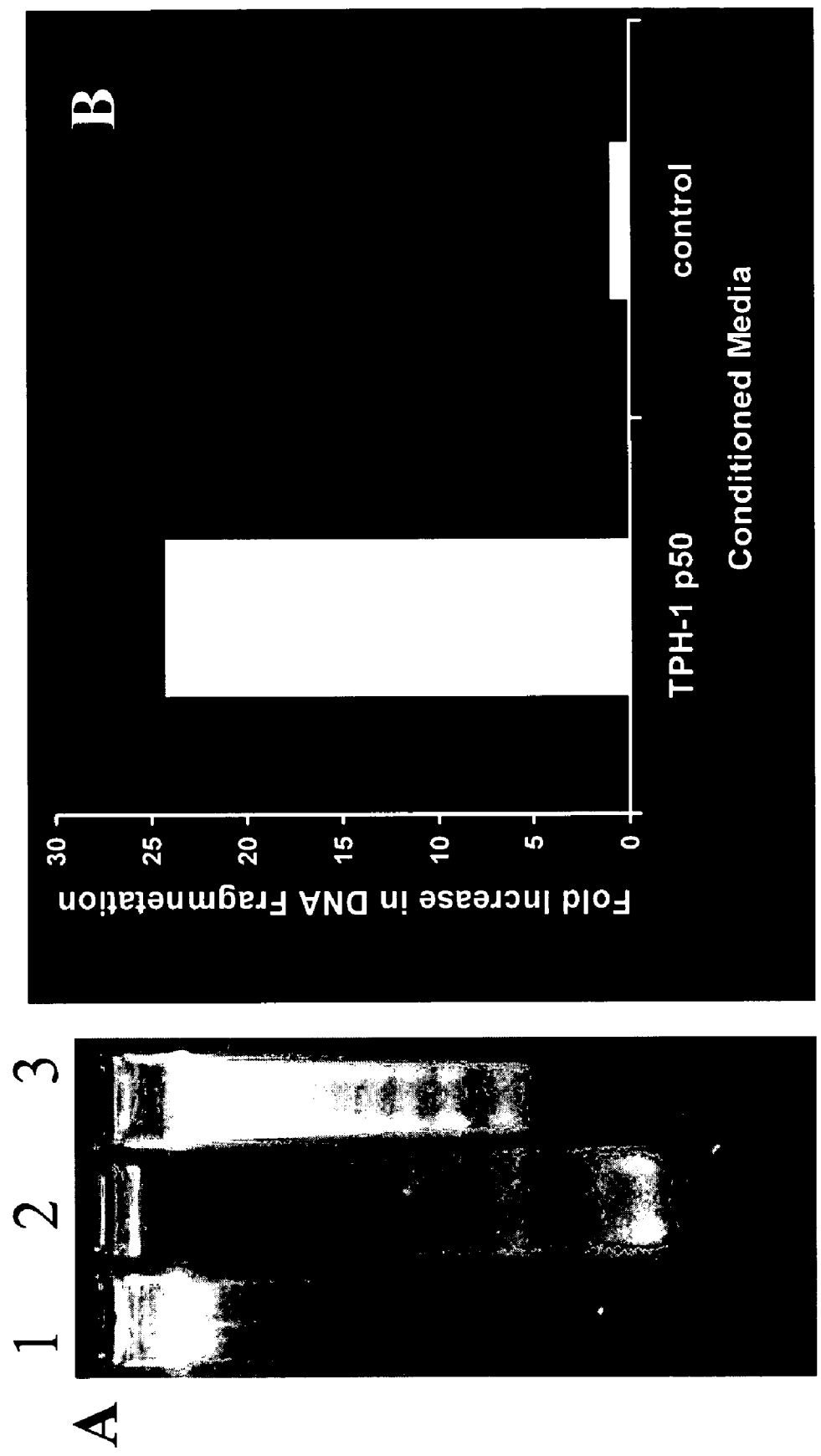
FIG. 3: Apoptosis of activated human liver stellate cells ("LX2 cells") by conditioned medium. Panel A: Analysis of DNA fragmentation in" LX2 cells incubated with conditioned medium from THLE cells as a negative control (lane 1), THLE-core (lane 2), and from TPH (lane 3). Panel B: Quantification of DNA fragmentation in LX2 cells upon incubation with conditioned medium from TPH-1, passage 50 or THLE (negative control). DNA fragmentation was quantified from cytosolic oligonucleotides-bound DNA using ELISA (Roche).

To determine how stellate cell death occurs, cells were harvested on day 6 and examined for characteristic DNA ladder of apoptosis. DNA from rat and human HSC incubated with the CM from TPH or THLE-core displayed apoptotic signature oligonucleosome fragments by agarose gel electrophoresis (FIG. 3, panel A). The level of apoptosis in LX-2 cells was also quantified by a cell death detection ELISA, which is based on the quantitative sandwich-immunoassay principle using mouse monoclonal antibodies against DNA and histone. This allows for the specific determination of oligonucleosomes in the cytoplasmic fraction of the apoptotic cells. Analysis of the LX-2 cells incubated with the CM from TPH or THLE-core suggested a significant level of apoptotic cell death as compared to the LX2 cells incubated in normal medium or conditioned medium from negative control THLE cells (FIG. 3, panel B).

EXAMPLE 2

Methods of Immortalizing Hepatocytes

Methods of producing immortalized hepatocytes for use in producing the conditioned media of the instant invention, are described in detail in Ray et al., 2000, and Basu et al., 2002, which are herein incorporated in their entirety by reference. A exemplary method is summarized below.

Cell growth regulatory potential of HCV core protein was investigated by introduction of the core genomic region into primary human hepatocytes, a natural host for virus replication and tropism (Ray et al., 2000). Interestingly, core transfected primary human hepatocytes (TPH) were immortalized and exhibited continuous growth for more than three years. In contrast, similar transfection with core deletion mutants (Core aa 26-85 and Core aa 80-150 or gene encoding nucleocapsid protein (NP) from an unrelated human parainfluenza type 3 virus (HPIV-3) as controls did not immortalize primary human hepatocytes. We have so far established immortalized hepatocytes from 3 different healthy donors and cells from another donor became contaminated by yeast and we could not recover cells from that culture.

Core transfected immortalized hepatocytes exhibited HCV core protein expression, albumin secretion, glucose phosphatase activity, and absence of smooth muscle actin (Ray et al., 2000). Cells in culture displayed focal cytoplasmic and membrane staining with a polyclonal anti-CEA (Dako rabbit anti-human CEA, A 0015), which has specificity for a range of related cell adhesion glycoproteins including carcinoembryonic antigen (CEA), biliary glycoprotein (BGP1/CEACAM1), and nonspecific cross reacting antigen (NCA/CEACAM6).

RNA extracted from the immortalized hepatocytes was examined for hepatobiliary transport marker genes. Three sets of sense and antisense oligonucleotide primers (Zollner et at, 2001) were used for detection of mRNA of multidrug resistance-associated protein (MRP), liver-specific organic anion transporter (LST1), and human Na+-taurocholate cotransporting polypeptide (NTCP). Primer sequences were selected from the respective cDNA sequences submitted in the GenBank (accession numbers ABOIO887, AFO60500 and L21893).

MRP-2 sense primer: CACCTTAGTGCAGCGCTTCTA (SEQ ID NO:10)

MRP-2 antisense primer: AGGTCTCTCAGCACCAG-GTCTAGG (SEQ ID NO:11)

NTCP sense primer: AACGCGTCTGCCCCATTCAAC (SEQ ID NO:12)

NTCP antisense primer: GACGGCCACACTGCACAA-GAGA (SEQ ID NO:13)

LST-1 sense primer: GAAGATGTTCTTGGCAGCTCT (SEQ ID NO:14)

LST-1 antisense primer: GATCCCAGGGTAAAGC-CAAT (SEQ ID NO:15)

Identical quantities of RNA were subjected to RT-PCR (BRL) using specific primers for amplification (~600 bp long). The amplified DNAs were subjected to gel electrophoresis. The relative abundance of MRP-2 and LST-1 was significantly higher than NTCP in immortalized cells under our experimental conditions. RNA from human foreskin fibroblasts was used as a negative control in this experiment and did not exhibit amplification of the specific bands. Results from this set of experiments further suggested the presence of hepatocyte specific markers in the immortalized cells.

An enhancement of telomere length, a characteristic of immortalized or transformed cells, was evident upon passage of the immortalized hepatocytes (Ray et al., 2000). Results from these studies suggested that HCV core protein promotes immortalization of primary human hepatocytes, which may predispose cells for transformation.

We also examined whether suppression of core genomic sequence has an effect upon the maintenance of immortalized hepatocytes and if there are any corresponding consequences on cellular gene expression. Results from these studies suggested that antisense RNA-mediated reduction of core protein function, at an early stage after hepatocyte immortalization, results in cell death. This might occur by regulation of cell cycle related genes, possibly by elevating p53 expression level (Basu et al., 2002). These results further demonstrated that hepatocyte immortalization is not due to an artifact of spontaneous clonal selection. However, antisense core gene expression did not exhibit apoptotic cell death in immortalized hepatocytes from late passage.

EXAMPLE 3

Purification and Identification of Stellate Cell Death Factor

Media conditioned by immortalized hepatocytes (supra) were concentrated, then diluted with four volumes of buffer H (20 mM Hepes, pH 7.4, 15% glycerol), and loaded onto a 2 ml Q-SEPHAROSE anion exchange column that had been pre-equilibrated with buffer H. The flow through was collected and loaded directed onto a 2 ml SP-column. After washing the column with 5 ml of buffer H, the bound protein was eluted with 5 ml of buffer H containing 0.5 M NaCl. 1 ml fractions were collected, analyzed by the stellate cell based apoptosis assay (supra) as well as SDS-PAGE, followed by Coomassie Blue staining. One major band was observed in the active fraction. That band was subjected to N-terminal micro sequencing, revealing both albumin and fetuin sequences (SEQ ID NO:9 and SEQ ID NO:1, respectively).

Figure 4:
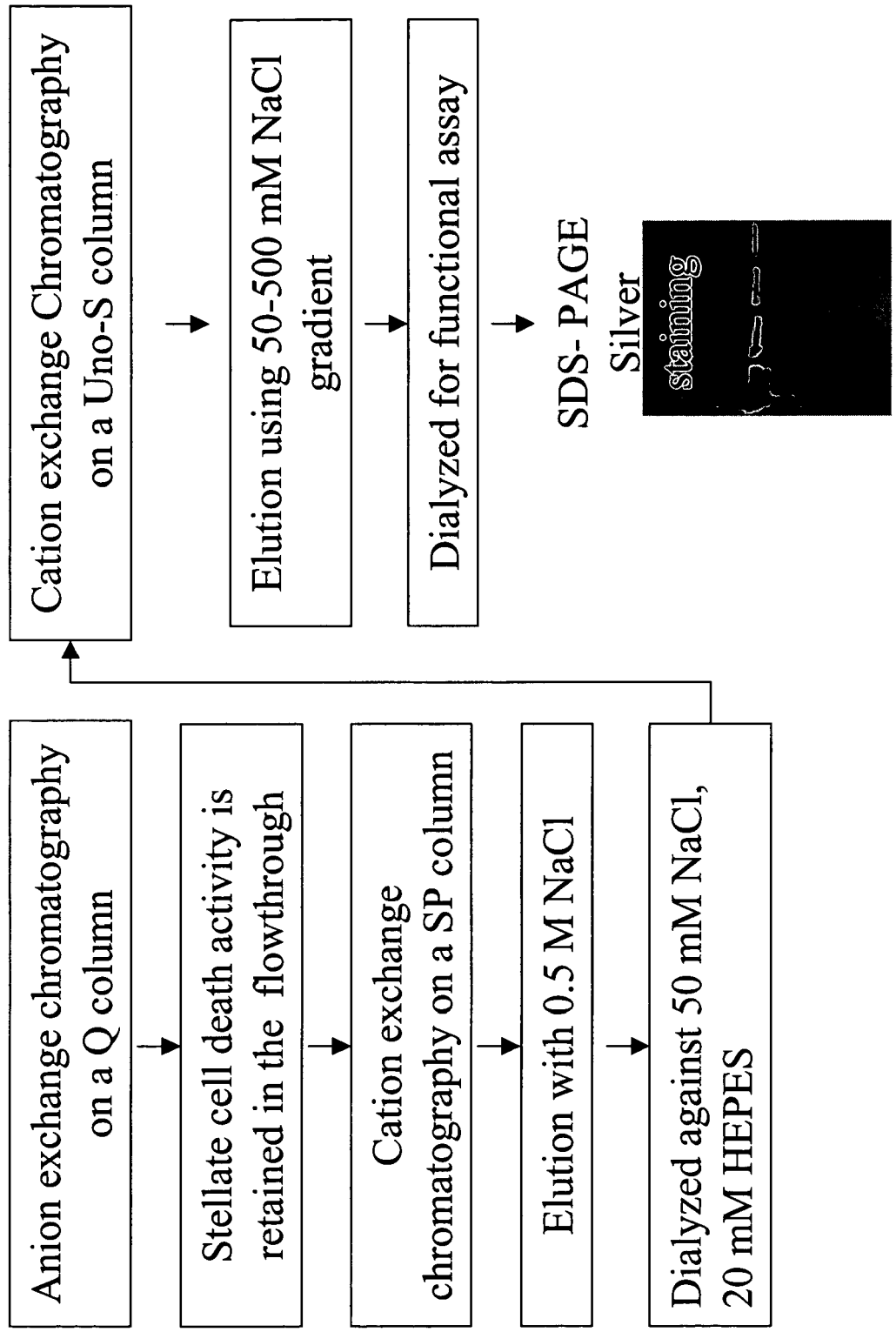
FIG. 4: Depiction of a representative protocol for purifying the pro-apoptotic activity from conditioned medium.

To ensure that this is indeed the protein that leads to cell death, the fractions eluted from the SP-column were pooled and dialyzed against buffer H (3×500 ml), and loaded on to UNO-S FPLC column. The bound protein was eluted with a liner gradient of 0-0.5M NaCl in 20 ml of buffer H with flow rate of 1 ml/min. Each fraction was analyzed by SDS-PAGE followed by silver staining, and only one major band was observed (FIG. 4). Each fraction was also subject to the stellate cell apoptosis assay.

EXAMPLE 4

Induction of TRAIL-Mediated Apoptosis

Activated HSCs are central to the pathogenesis of liver fibrosis/cirrhosis, both as a source of fibrillar collagens that characterize fibrosis/cirrhosis and tissue inhibitors of matrix degrading metalloproteinases (TIMPs). Moreover, activated HSC apoptosis plays a critical role in the spontaneous recovery from biliary fibrosis (Issa et al; 2001). Both survival and apoptosis of HSC are regulated by growth factors expressed during fibrotic liver injury. We have previously shown that HCV core protein mediates immortalization of primary human hepatocytes, a natural host for virus replication and tropism (Ray et al 2000). In this study, we investigated the relationship between HCV core protein mediated immortalized hepatocytes (IH) and activated HSC. To study the relationship between the IH and activated HSCs, we used a spontaneously immortalized human stellate cell line (LX2) and primary rat HSCs. These two different cells were co-cultured and examined for cell growth. IH preferentially grew and suppressed proliferation of activated LX-2 cells. The number of LX2 cells decreased by >90% within 96 hours. The LX2 cells and IH were identified by immunofluorescence using anti-SMA antibody, and a hepatocyte specific monoclonal antibody. The suppression of activated stellate cell growth could be due to a higher growth rate of the IH or due to the regulation of activated HSCs by the immortalized hepatocytes either through a receptor interacting protein-dependent mechanism, or by secretion of a soluble mediator.

Figure 5:
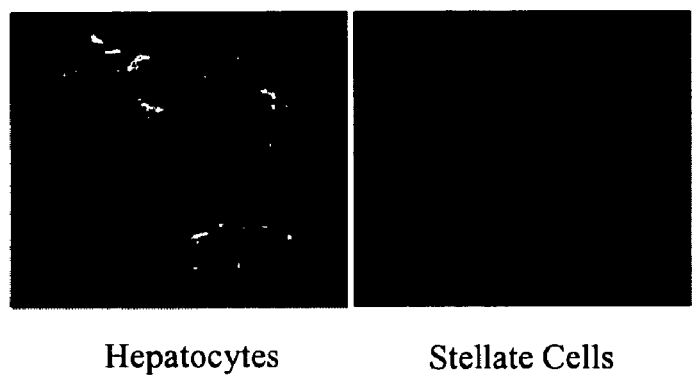
FIG. 5: Panel A: Identification of HCV core transfected primary human hepatocytes and stellate cells in culture. Hepatocytes were identified by indirect immunofluorescence with a specific MAb Hep Par. Activated stellate cells were identified using a MAb to α-smooth muscle actin. Effect of soluble mediator in conditioned medium of IPH on stellate cell growth. Panel B: LX2 cells were treated with CM from early (#-#) and late passage (>-->) IPH. LX2 cells were similarly treated with SABM (!-!) for comparison. Rat stellate cells were similarly treated with CM from IPH cells (#-#). Rat stellate cells were similarly treated with SABM (!-!) for comparison. Cell viability was assessed from triplicate culture wells by CellTiter 96 Aqueous non-radioactive cell proliferation kit (Promega) at different time points and presented as mean values. Panel C: Conditioned medium from IPH exhibited a dose dependent effect on LX-2 cell viability.
Figure 5:
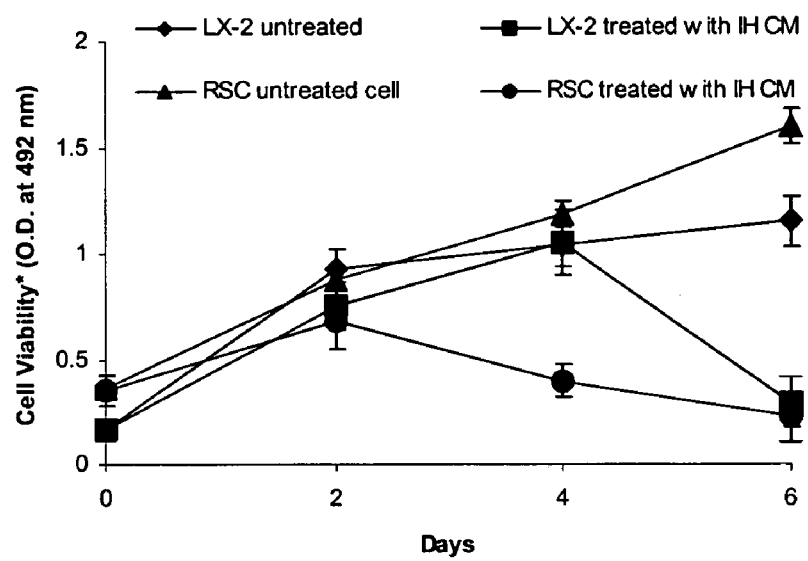
Figure 5:
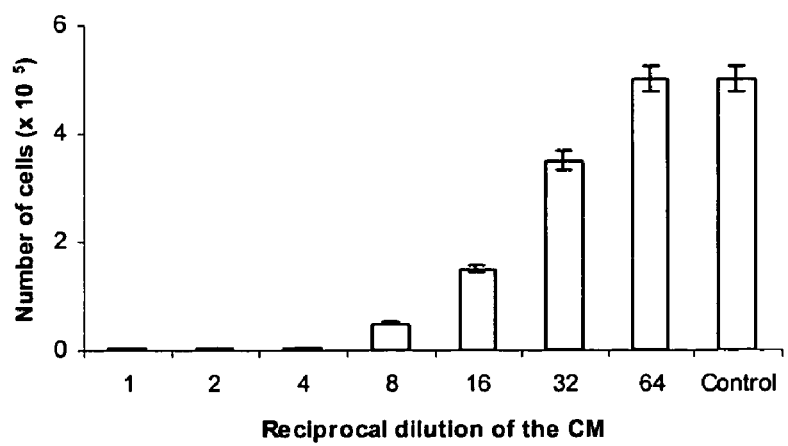

We have previously investigated the cell growth regulatory potential of HCV core protein by introduction of the core genomic region into primary human hepatocytes, a natural host for virus replication and tropism (Ray et al 2000). During that study, at ~6-8 weeks after transfection, hepatocytes exhibited a shift from senescence to a replicative stage. The growth of the hepatocytes were examined by immunofluorescence using a hepatocyte specific monoclonal antibody Hep Par (FIG. 5, panel A). Primary hepatocyte preparations generally contain a small percentage of contaminating stellate cells. Activated hepatic stellate cells (HSC) were also observed in the transfected hepatocyte culture by immunofluorescence, and were observed to be present 6-8 weeks after transfection using an antibody against smooth muscle actin (SMA), a marker for activated stellate cells (FIG. 5, panel A). Interestingly, when core transfected primary hepatocytes entered from senescence to replicative stage, they preferentially grew, and replaced the activated HSCs, which could not be detected within 4 weeks of this shift.

To further investigate whether the suppression of activated LX2 cell proliferation by IH was through a receptor interacting mechanism or through a soluble mediator, we cultured the LX2 and IH on either side of a dual chamber in a trans well dish separated by a 0.45 μm filter. IH suppressed the proliferation of the activated LX2 cells indicating that IH might be secreting a soluble mediator into the culture medium to suppress LX2 cell proliferation. To further verify our result, we incubated LX2 cells with conditioned medium (CM) from the IH. LX-2 or rat HSCs became granular upon incubation with CM, and complete disruption of the cell monolayer with suppression of cell proliferation was observed between 2-4 days of incubation (FIG. 5 panel B). These results indicated that the soluble mediator in culture medium from IH may not be species specific for stellate cells. The activity of CM on LX-2 growth control proportionately decreased with increasing dilutions of the CM. (FIG. 5, panel C). We also examined the viability of HSC from disrupted monolayer by trypan blue dye exclusion. Majority of the disrupted cells from monolayer (>90%) retained trypan blue stain indicating cell death. We also examined the role of CM on hepatic (Huh-7, and THLE) and non-hepatic (HeLa, MCF-7, and BHK) cell growth. Growth suppression was not observed with any one of these cell lines, indicating that soluble mediator from IH acts specifically on hepatic stellate cells. Together, our results indicated that IH secrete a soluble mediator that causes LX2 cell death.

To investigate whether other immortalized cell types secrete death factor, we incubated LX2 cells with the CM from non-hepatic (HeLa, MCF-7, BHK, CHO) and hepatic (HepG2, Hep3B, Huh-7 and THLE) cell lines. LX2 growth suppression was not observed with CM from non-hepatic and two of the hepatic cell lines (THLE and Huh-7). However, CM from HepG2 or Hep3B cells induced LX2 cell growth suppression death in a manner similar to IH. Both HepG2 and Hep3B are transformed human hepatocytes. These observations indicated that the soluble mediator, released in conditioned medium, was not limited to some of the transformed hepatocytes, but is not due to solely to the presence of HCV core protein.

Figure 6:
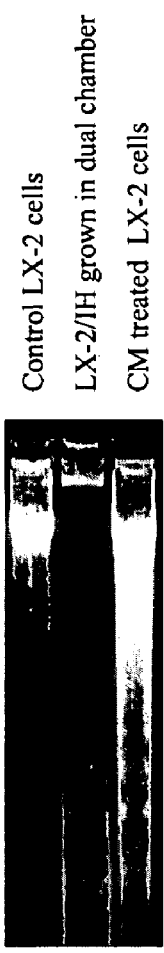
FIG. 6: Panel A: Soluble mediator from IPH induces apoptosis in LX2 cells. Analysis for DNA fragmentation of LX2 cells following treatment with SABM (lane 1), CM from late passage IPH (lane 2) or after culture of LX2 and IPH in dual chamber trans well dish (lane 3). DNA extracted from cells was analyzed by 1.6% agarose gel electrophoresis. Panel B: Quantitation of DNA fragmentation in LX2 cells. CM from IPH or SABM treated LX2 cells were analyzed for cytosolic oligonucleosome-bound DNA by ELISA (Roche).
Figure 6:
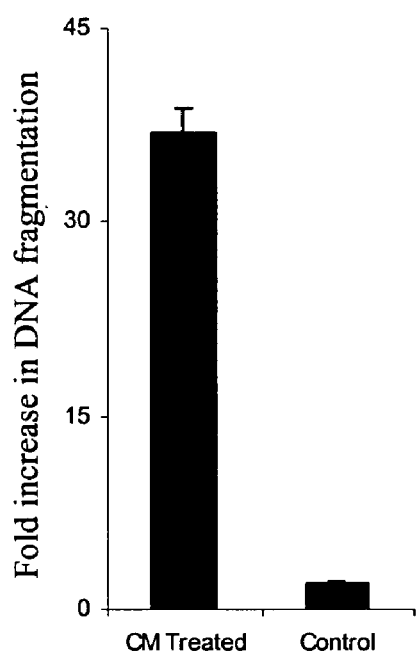

To determine whether the observed LX2 cell death was associated with apoptosis, LX2 cells were incubated with the CM from IH or cocultured with IH in a dual chamber. LX2 cells harvested after 4 days of incubation with IH, displayed apoptotic signature oligonucleosome fragments by agarose gel electrophoresis (FIG. 6, panel A). DNA fragmentation of LX-2 cells was quantified by a cell death detection ELISA, which is based on the quantitative sandwich-immunoassay principle using mouse monoclonal antibodies against DNA and histone. This allows for the specific determination of oligonucleosomes in the cytoplasmic fraction of the apoptotic cells. ELISA with LX-2 cells, prior incubated with the CM from IH or cocultured with IH in dual chambers, suggested a significant increase (40 fold) of apoptotic cell death as compared to LX2 cells incubated with culture medium (FIG. 6, panel B).

To identify the soluble mediator, we compared the cytokine expression profile of the CM from IH and THLE (which does not cause LX-2 apoptosis) using multiple human cytokine array. An increase of ~10 fold in TIMP-1, ~4 fold of TIMP-2, and ~2 fold each of FGF-9, IGFBP-4, and osteoprotegrin levels were observed in the CM from IH (Table 2). On the other hand, the levels of interleukins and TNF related cytokines (TGF-β, TNF-α TNF-β, and IGF-1) remained similar in the CM of IH and THLE, indicating that these cytokines are not responsible for LX-2 cell apoptosis (Table 2). We have observed that the activity of the soluble modulator from IH causing LX-2 cell death is lost upon incubation at 56° C. for 5 minutes.

TABLE 2

Cytokine profile of the CM from IH relative to CM from THLE cells

| Functional gene grouping | Fold change |
| --- | --- |
| Interleukins | |
| IL-1, IL-2, IL-3, IL-4, IL-5, IL-6, IL-7, IL-8, IL-10 IL-12, IL-16 | No change |
| TNF related cytokines | |
| TGF- β, TNF-α TNF-β, IGF-I | No change |
| EGF/FGF | |
| EGF, FGF-4, FGF-6, FGF-7 | No Change |
| FGF-9 | +2 |
| TIMP Family | |
| TIMP-1 | +10 |
| TIMP-2 | +4 |
| IGFBP Family | |
| IGFBP-1, IGFBP-2, IGFBP-3 | No change |
| IGFBP-4 | +2 |
| Others | |
| Osteoprotegrin | +2 |
| RANTES | No change |

Figure 7:
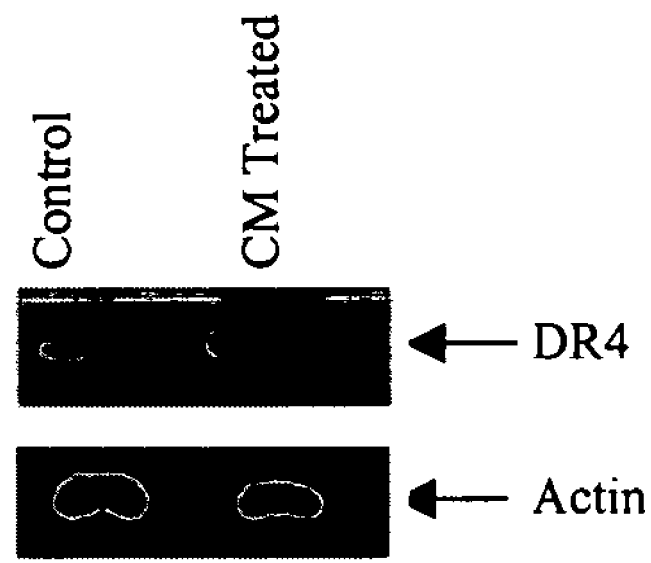
FIG. 7: Expression level of DR4 (panel A), DR5 (panel B), in IPH CM treated LX2 cells and in control cells. The level of cellular actin was used as an internal control. Arrows on the right indicate respective proteins. Molecular weights of the respective proteins were verified from the position of prestained molecular weight markers (Invitrogen).
Figure 7:
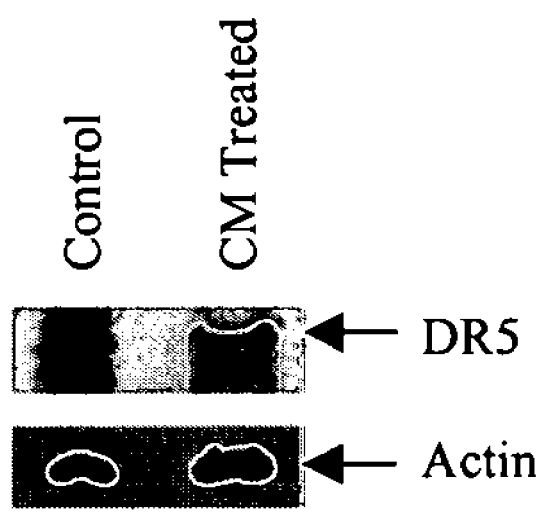

Among the extrinsic apoptotic pathways, FAS and TNF-α were not utilized by the soluble mediator to induce apoptosis in LX2 cell since addtion of anti-Fas Ab or TNF-α did not induced apoptosis of LX-2 cells. However, the addition of histidine tagged rhTRAIL along with anti-polyhistidine antibody induced apoptosis of LX-2 cells. Therefore, we examined whether the soluble mediator utilizes the TRAIL pathway to induce apoptosis. TRAIL induced apoptosis can often lead to an increase in expression of TRAIL receptors (Zhang et al. 1999; Wang and El-Diery, Oncogene, 22, 8628). We first examined whether the TRAIL receptors are modulated in LX2 cells upon incubation with CM and observed an upregulation of DR4 (TRAIL-R1) and DR5 (TRAIL-R2) expression. Densitometric scanning suggested an ~4 fold increase in the individual expression of DR4 and DR5 (FIG. 7, panels A and B). These findings suggested that the soluble mediator in CM may be targeting TRAIL pathway to induced apoptosis in LX-2 cells. Surprisingly, the treatment of CM from IH with neutralizing antibodies to TRAIL did not inhibit LX-2 cell apoptosis. Similar observations were also reported by Fisher et al. (2002), during stellate cell killing by activated Kupffer cells. Activated Kupffer cells induce apoptosis of HSCs through upregulation of the DR4 and DR5 receptors, although the addition of the neutralizing antibodies to TRAIL did not inhibit HSC apoptosis. Thus, the soluble mediator in the CM of IH induces apoptosis of LX-2 cells by utilizing TRAIL receptors.

Figure 8:
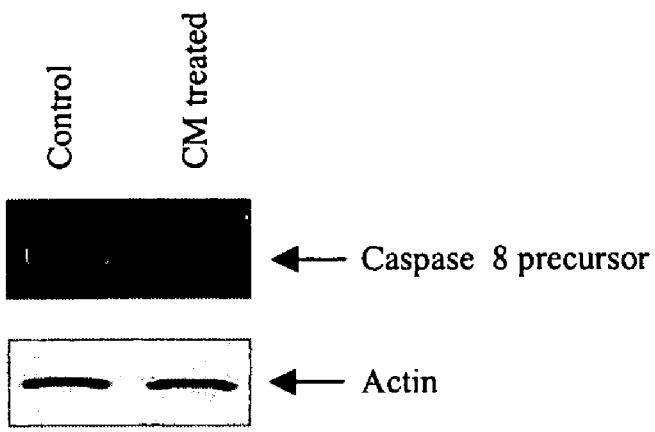
FIG. 8: Expression status of caspase 8 (panel A), Bax and Bcl (panel B) in control and CM treated LX2 cells. Cellular actin was used as an internal control to verify the level of protein load in each lane. Arrows on the right indicate respective proteins. The molecular weights of the respective protein bands were verified from the position of prestained molecular weight markers (Invitrogen).
Figure 8:
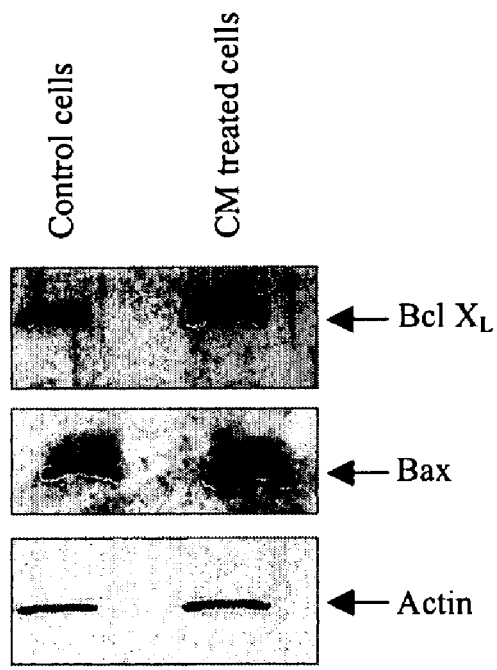
Figure 9:
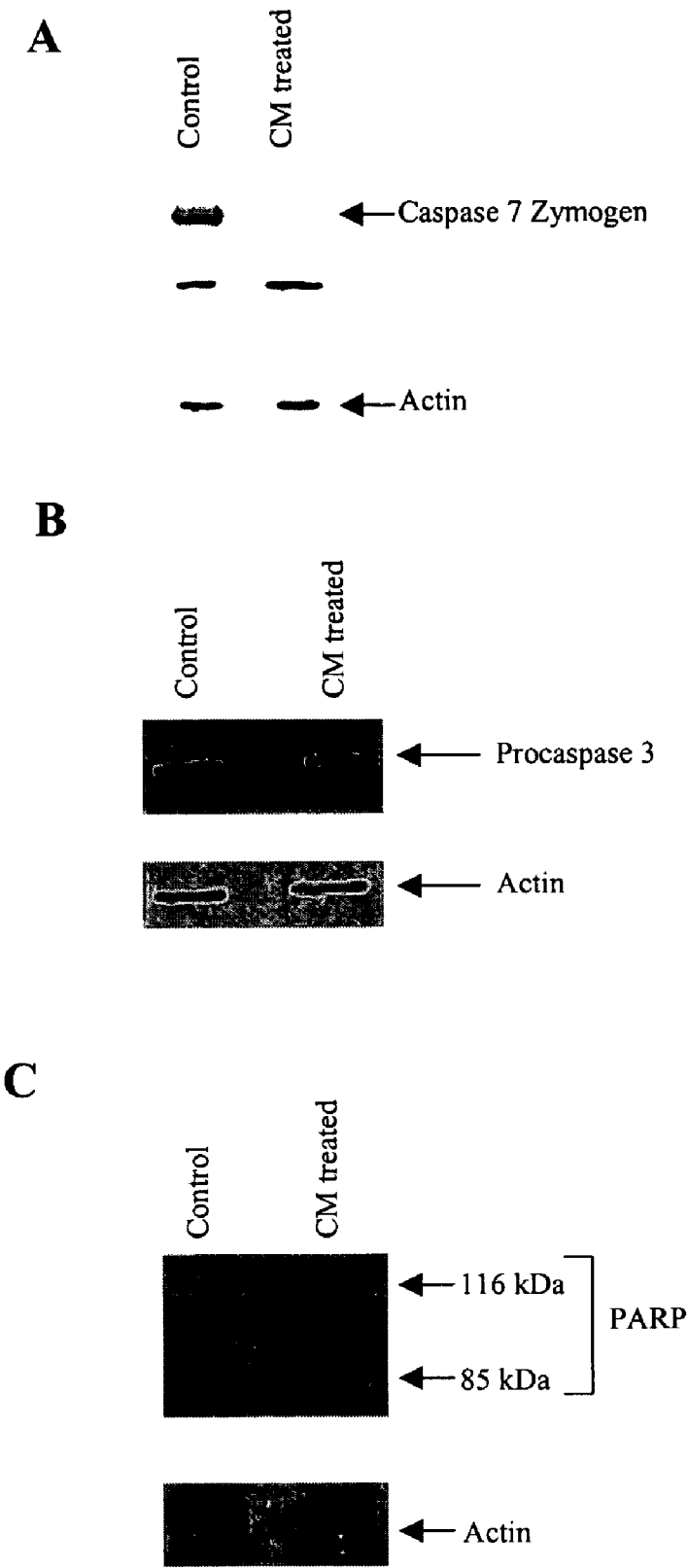
FIG. 9: Expression status of caspase 7 (panel A), pro-caspase 3 (panel B) and PARP (panel C). Cellular actin was used as an internal control to verify the level of protein load in each lane. Arrows on the right indicate respective proteins. The molecular weights of the respective protein bands were verified from the position of prestained molecular weight markers (Invitrogen).

To further investigate the apoptotic signaling pathway we analyzed caspase activation and PARP cleavage in CM treated LX-2 cells by Western blot. Decrease in the expression of procaspase 8 in CM treated LX-2 cells as compared to untreated cells suggested the activation of procaspase 8 in CM treated LX-2 cells (FIG. 8, panel A). However, activation of caspase 9 was not observed in the control or CM treated cells. Caspases 3, 7 and PARP play a key role in the final or execution phase of apoptosis. The cell lysates were similarly subjected to Western blot analysis for detection of caspases 3, 7, and PARP cleavage. Activation of caspase 7 (FIG. 9, panel A), not caspase 3 (FIG. 9, panel B) was observed. Furthermore, cleavage of the DNA repair enzyme PARP was similarly examined. The 116 kDa polypeptide was cleaved to ~86 kDa signature peptide upon treatment of LX2 cells with CM (FIG. 9, panel C).

Figure 10:
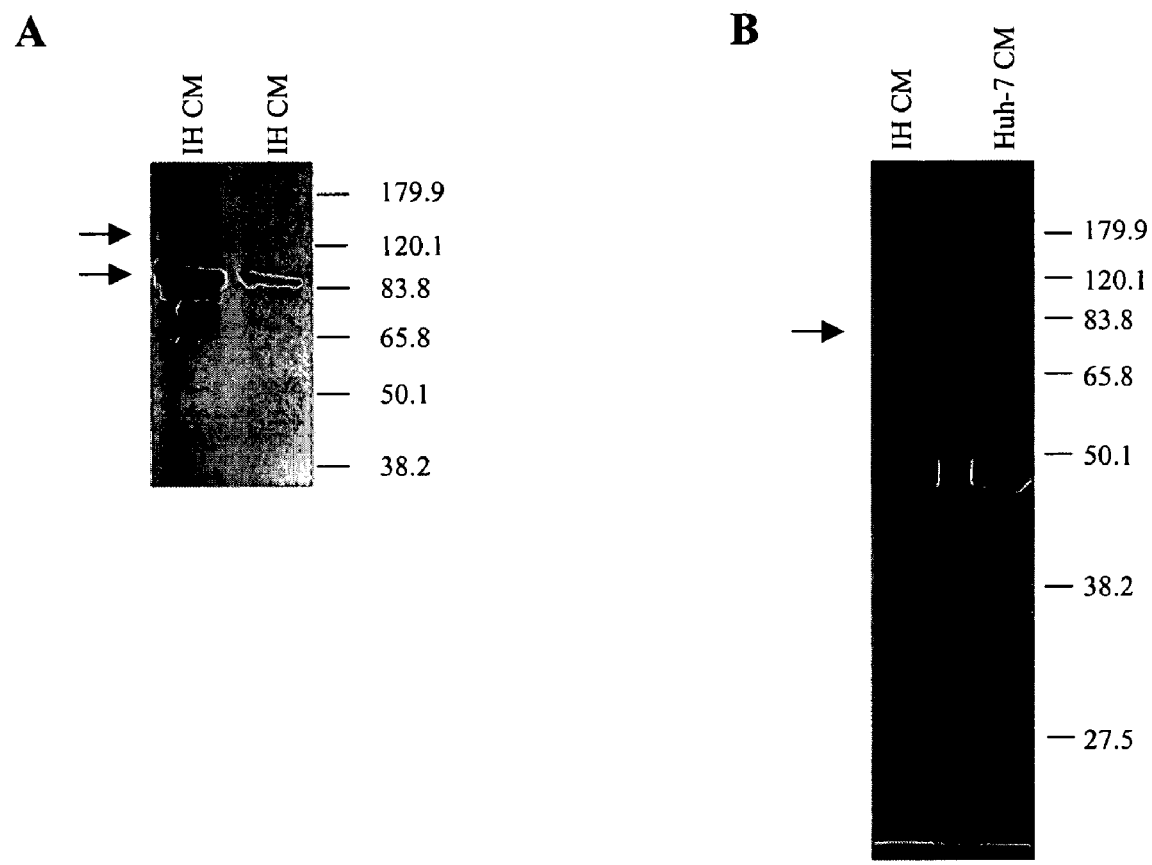
FIG. 10. Characterization of stellate cell death factor from hepatocyte conditioned medium of IH cells. Migration of the purified stellate cell death factor from the active fractions eluted from the SP-column, on SDS-PAGE (Panel A). The cell supernatant was collected from log phase of growing cells, enriched and active fractions were analyzed by 8.5% SDS PAGE under reducing conditions. Arrows on the left indicate the two forms. Molecular weights were ascertained from the positions of a prestained molecular weight marker (Invitrogen) run on the same gel. Functionally inactive fractions did not exhibit a detectable polypeptide band. Co-inmiunoprecipitation with BSA (Panel B). Inventors also found that the stellate cell death factor could be co-immunoprecipitated from the cell-supernatant of IH cells (left) but not Huh-7 cells (right) using antibody to BSA.

The apoptosis inducing soluble mediator from serum free CM of IH was purified by a four-step process (described in the materials and methods section). Following each step, the isolated fractions were tested for their ability to induce apoptosis on LX2 cells. The fractions showing apoptosis were pooled and subjected to purification. Active fractions after the last step of purification were analyzed by SDS-PAGE, and silver staining for purity and molecular weight determination. A major polypeptide band of ~80 kDa (p80) and a minor band of ~120 kDa (p120) were observed (FIG. 10, panel A). Functionally inactive fractions did not exhibit a detectable polypeptide band. Both the bands were subjected to Edmann degradation for N-terminal micro sequencing. Amino acids from microsequencing revealed similar N-terminal amino acid residues for both ~80 kDa and ~120 kDa. Both the bands were found to be a mixture of two proteins (DTHKSEIAHR+IPLDPVAGYK, SEQ ID NO:9 and SEQ ID NO:1, respectively) and their amino acid sequence revealed identity with the amino terminal sequence of BSA (DTHKSEIAHR; SEQ ID NO:9) and bovine α-HSP (IPLDPVAGYK; SEQ ID NO:1) deposited in GenBank.

Human α-2HS glycoprotein has ~60% homology with bovine α-2HS glycoprotein, with complete mismatch in the first 10 N-terminal amino acid residues. Also, there are reports that human α-2HS glycoprotein (human feutin) can induce apoptosis under certain conditions and have anticancer activity (Yu, C-L; Cancer letters. 2001, 166; 173-184). To investigate whether the protein is a different variant of the human α-2HS glycoprotein, the CM and its active fractions from purification steps were treated with a neutralizing antibody to human α-2HS glycoprotein, prior to incubation with LX2 cells. Treatment of the CM or the active fractions did not inhibit stellate cell death activity. These results indicated that the soluble factor is not the human α-2HS glycoprotein. Similarly addition of BSA to culture medium did not induce apoptosis. Interestingly, the CM failed to induce apoptosis upon treatment with albumin. We also found out that the soluble mediator could be co-immunoprecipitated from the medium using antibody to BSA (FIG. 10, panel B). This result also suggested that most probably the soluble mediator forms a tight complex with BSA.

To further prove that this p80 is responsible for the apoptosis of the LX2 cells, the IH, HepG2 and Huh-7 cells were plated in 35-mm plates to about ~90% confluency and were metabolically labeled with $^{35}$S-protein labeling mix. The cell supernatant was collected after 24 h of culture, clarified, concentrated, and analyzed by SDS-PAGE. An ~80 kDa band was observed in the cell supernatant of the IH and HepG2 cells, but not in the CM from Huh-7 cells which did not induce apoptosis of LX2 cells. MALDI-TOF/MS analyses of the purified soluble mediator did not match with the existing database.

Materials and Methods

HCV core immortalized human hepatocytes (IH) were generated by transfection of primary human hepatocytes with the plasmid DNA expressing core genomic region of genotype 1a (Ray et al, 2000). Transfected hepatocytes were seeded on a collagen type I coated plate and maintained at 37° C. in a defined culture medium supplemented with growth factors and antimicrobial agents (SAGM, Clonetics, Walkersville Md.), or with DMEM supplemented with 5% FBS.

A spontaneously immortalized human stellate cell line (LX-2) was kindly provided by Dr. Scott L. Friedman (Mount Sinai School of Medicine, NY). LX-2 cells are a low-passaged human cell line derived from normal human stellate cells that are spontaneously immortalized. These cells were selected by their ability to grow under low serum conditions (1% fetal bovine serum) and express α-SMA under all culture conditions (Taimr, P. Hepatology, January 2003, Volume 37, Number 1). LX-2 cells were grown in activated state on plastic dishes, in Dulbecco's minimum essential medium (DMEM; BioWhittaker, Walkersville, Md.) supplemented with 5% fetal bovine serum, 100 U/mL penicillin, 100 μg/mL streptomycin, 2× L-glutamine. LX2 cells also grew in defined culture medium for immortalized hepatocytes when supplemented with 2× glutamine. Primary stellate cells from rat liver (kindly provided from the laboratory of Dr. Bruce Bacon, Saint Louis University) were grown in Dulbecco's medium supplemented with 10% fetal bovine serum.

Monoclonal and polyclonal antibodies to caspases 3, 7, hTRAIL and poly histidine were obtained from R&D Systems (Mineapolis, Minn.), caspase 9, Fas, Fas-L were obtained from Pharmingen (SanDiego, Calif.), while antibodies to PARP, DR4, DR5 and caspases 8 were obtained from Alexis Biochemicals (Carlsbad, Calif.). rhTNF-α and recombinant hTRAIL were obtained from Promega and R&D Systems.

LX2 and IH were cocultured for 3 days under conditions permitting either cell-to-cell contact or in transwell chambers. The ratio of IH to LX2 at the onset of culture was 1:1. For coculture, LX2 and IH cells were grown for 2-4 days in SAGM (Clonetics Walkersville, Md.) supplemented with 2× glutamine and 5% chemically denatured serum (BioSource, Md.). Cocultures were also performed in Transwell dual chambers (Costar). The two compartments were separated by a porous polycarbonate membrane (0.45 μm pore diameter), which allows free exchange of soluble factors between the two compartments. In transwell chambers, IH cells were seeded in the upper compartment while the bottom compartment contained LX2 cells.

LX2 and IH were identified by immunofluorescence using activated HSC specific anti-smooth muscle actin antibody (Sigma, St. Louis, Mo.) and hepatocytes specific monoclonal antibody (DAKO, Carpinterin, Calif.). Briefly, cells were grown on cover slips, washed with PBS, and fixed with 10% formaldehyde for 15 minutes at room temperature. Fixed cells were incubated for 1 h with a mouse monoclonal antibody to α-smooth muscle actin or hepatocyte specific antibody at appropriate dilutions. Cells were extensively washed and incubated for 1 h with FITC-conjugated anti-mouse IgG. Control cells were processed similarly without incubation with the first antibody. Cover slips were mounted in anti-fade reagent, and the cells were observed using a fluorescence microscope.

IH were grown on a collagen type 1 coated plate in SAGM supplemented with 5% chemically denatured serum at 37° C. At ~80-90% confluency, cells were washed extensively and incubated with serum free SAGM. The culture medium was collected as conditioned medium (CM) from IH after 48 hours. CM was clarified by centrifugation at 6,000 g to remove cell debris, supplemented with 2× L-glutamine, and aliquoted for storage at −20° C. until use. Conditioned medium from HeLa, MCF-7, BHK, CHO, HepG2, Hep3B and Huh-7 cells, maintained in Dulbecco's essential medium supplemented with 10% fetal calf serum, were prepared in a similar manner.

LX2 and rat HSC prolliferation were assessed using a CellTiter 96 Aqueous non-radioactive cell proliferation assay (Promega, Madison, Wis.). This assay is composed of a novel tetrazolium compound [3-(4,5-dimethylthiazol-2-yl)-5-(3-carboxy methoxyphenyl)-2-(4-sulphophenyl)-2H-tetrazolium, inner salt, MTS] and an electron coupling reagent (phenazine methosulfate; PMS). MTS is bioreduced by cells into formazan, that is soluble in cell culture medium. The conversion of MTS into aqueous, soluble formazan is accomplished by a dehydrogenase enzyme found in metabolically active cells. Thus, the quantity of formazan produced in cell culture medium is directly proportional to the number of living cells. After 2 days of culture in a 96 well plate, LX2 cells were incubated with CM from IH. LX2 cells were harvested at different time points and their growth were compared with cells grown in serum free SAGM, supplemented with 2× L-glutamine.

IH, HepG2 and Huh-7 cells were grown in 35-mm plates to ~90% confluency. Cell monolayers were washed with medium lacking methionine and cysteine and incubated in the same medium for an additional 30 min. The cells were then incubated in medium containing 50 μCi/ml of $^{35}$S-protein labeling mix (Amersham) for 18 hours. Cell culture supernatant was collected after 24 h, centrifuged to remove cell debris and was concentrated using a membrane filter with exclusion limit >50 kDa proteins (Millipore, Bedford, Mass.). The concentrated supernatant was mixed with equal amounts of sample buffer (2×) and analyzed by 8.5% SDS-PAGE.

RayBio™ human cytokine array (RayBio™, Atlanta, Ga.) was used to identify the expression profile of multiple cytokines following the manufacturer's procedure. Briefly, CM from IH and a different human hepatocyte cell line (THLE, immortalized by SV40 T antigen kindly provided by Curtis C. Harris, NCI) were concentrated and incubated with the protein array membrane containing antibody against the cytokines. Following incubation, the membrane was washed and developed by the addition of horse radish peroxidase conjugated streptavidin and substrate, followed by chemiluminescence. The image from the membrane exposed to X-ray film was scanned to quantitate cytokine levels using a densitometric scanner after normalizing with the controls.

Western blot analysis was performed to analyze the expression level of Bax, Bcl-XL, DR4, DR5, caspases 3, 7, 8 and 9 using specific antibodies in control and experimental cells. Briefly, equal amounts of whole cell lysates in sample buffer were separated by SDS-PAGE, and transferred onto nitrocellulose membrane. The separated proteins were incubated with specific antibody, followed by a HRP conjugated secondary antibody, and detected by chemiluminescence. Cellular actin was detected similarly in a reprobed blot for use as an internal control for relative quantitation of the proteins in control and experimental cells by densitometric scanning.

The concentrated CM (~20 fold) was first diluted with four volumes of buffer H (20 mM Hepes, pH 7.4, 15% glycerol), and loaded onto a 2 ml Q-SEPHAROSE anion exchange column that was pre equilibrated with buffer H. The flow through from the void volume of the column exhibited stellate cell cytotoxicity. This active fraction was subsequently loaded onto a 2 ml SP-column. After washing the column, bound protein was eluted with 5 ml of buffer H containing 0.5 M NaCl. Fractions (1 ml) were collected and evaluated for LX2 cell death assay, and protein in each fraction was analyzed by SDS-PAGE, followed by silver staining. Active fractions eluted from the SP-column were pooled, dialyzed against buffer H (3×500 ml), and loaded on to UNO-S FPLC column. The bound protein was eluted with a liner gradient of 0 to 0.5 M NaCl in 20 ml of buffer H with a flow rate of 1 ml/min. Each fraction was analyzed for LX2 cell death, as well as by SDS-PAGE and silver staining. The N-terminal amino acid sequencing was done by Midwest Analytical, Inc (St. Louis, Mo.) following Edman degradation.

MALDI-TOF/MS analysis of the purified soluble mediator was performed with a (Voyager DEPRO Perseptive) MALDI mass spectrometer. In brief, protein samples were solubilized for 30 min at ambient temperature in 9 M urea, 1% CHAPS, 70 mM dithiothreitol, 2% Servalyte pI 2-4 (Serva). For the resolution of protein samples a 10×12 cm gel electrophoresis system was used. For the identification of proteins 50-70 μg of proteins were applied to the sample template of a MALDI mass spectrometer (Voyager DEPRO, Perseptive). Peptide mass fingerprints were searched with the program MS-FIT (prospector.ucsf.edu/ucsfhtml/ms-fit.htm) using all cellular proteins in the NCBI data base allowing amass accuracy of 100 ppm for the peptide masses. Partial enzymatic cleavages leaving two cleavage sites, oxidation of methionine, pyroglutamic acid formation at the N-terminal glutamine, and modification of cysteine by acrylamide were considered in these searches.

REFERENCES

Applicants make no statement, inferred or direct, regarding the status of the following references as prior art.

Applicants reserve the right to challenge the veracity of any statements made in these references, which are incorporated herein by reference.

Abdel-Aziz, G, et al. 1990. Am J Pathol. 137: 1333-42.
Alcolado, R, M. J. Arthur and J. P. Iredale. 1997. Clin Sci (Lond). 92: 103-12.
Ashkenazi, A. 2002. Nat Rev Cancer. 2: 420-30.
Barco, A, E. Feduchi and L. Carrasco. 2000. Virology. 266: 352-60.
Basu et al., Virology 298:53-62 (2002).
Blanco, R, L. Carrasco and I. Ventoso. 2003. J Biol. Chem. 278: 1086-93.
Choo, Q. L., et al. 1989. Science. 244: 359-362.
Clarke, B. 1997. J. Gen. Virol. 78: 97-2410.
DiBisceglie, A. M., R. L. Cairithers, and G. J. Gores. 1998. Hepatology. 28: 1161-1165.
Du, C., et al. 2000. Cell. 102: 33-42.
Dufour, J. F., R. DeLellis, and M. M. Kaplan. 1997. Ann Intern Med. 127: 981-5.
Dufour, J. F, R. DeLellis, and M. M. Kaplan. 1998. Dig Dis Sci. 43: 2573-6.
Dziegielewska et al., J. BIOL. CHEM. 265:4354-4357 (1990).
Farci, P, et al. 1992. J Infect Dis. 165:1006-11.
Farci, P, et al. 1994. Proc Natl Acad Sci USA. 91:7792-6.
Fischer, R, et al. 2001. Gastroenterology. 120: 1212-26.
Fischer, R, et al. 2002. Gastroenterology. 123: 845-61.
Friedman, S. L, et al. 1985. Proc Natl Acad Sci USA. 82: 8681-5.
Friedman, S. L. 1993. N Engl J. Med. 328: 1828-35.
Friedman, S. L. 2000. J Biol. Chem. 275: 2247-50.
Ikeda, M, et al. 2003. Immunology. 108: 116-22.
Iordanov, M. S., et al. 2000. Cancer Res. 60: 1983-94.
Iredale, J. P, et al. 1998. J Clin Invest. 102: 538-49.
Iredale, J. P. 2001. Semin Liver Dis. 21: 427-36.
Issa R, et al. 2001. Gut. 48: 548-57.
Li, M. L, et al. 2002. Virology. 293: 386-95.
Maher, J J, and R. F. McGuire. 1990. J Clin Invest. 86: 1641-8.
Marchenko, N. D, A. Zaika and U. M. Moll. 2000. J Biol. Chem. 275: 16202-12.
McGee, J. O, anD R. S. Patrick. 1972. Lab Invest. 26: 429-40.
McGee, J, 0, and R. S. Patrick 1972. J Pathol. 106:Pvi.
McHutchison, J. G, et al. 1998. N Engl J. Med. 339, 1485-92.
Prikhod'ko, G. G, et al. 2002. J. Virol. 76: 5701-10.
Purcell, R. H. 1994. FEMS Microbiol Rev. 14: 181-91.
Purcell, R. H. 1994. Proc Natl Acad Sci USA. 91: 2401-6
Ray, R. B., K. Meyer, and R. Ray. 2000. Virology. 271:197-204.
Ray, R. B. and R. Ray. 2001. FEMS Mini Review. 202: 149-156.
Rehermann, B., and F. V. Chisari. 2000. Curr Top Microbiol Immunol. 242: 299-325.
Rockey D. C., et al. 1992. J Submicrosc Cytol Pathol. 24: 193-203.
Roos, R. W, and T. Medwick. 1980. J Chromatogr Sci. 18: 626-30.
Saile, B, et al. 1997. Am J Pathol. 151: 1265-72.
Saito, I., et al. 1990. Proc. Nad. Acad. Sci., USA. 87: 6547-6549.
Shafee, N, and S. AbuBakar. 2003. J Gen Virol. 84: 2191-5.
Srinivasula, S. M, et al. 2000. J Biol. Chem. 275: 36152-7.
Srinivasula, S. M, et al. 2001. Nature. 410:112-6.
Taimr, P, H. et al. 2003. Hepatology. 37: 87-95.
Verhagen, A. M, E. J. Coulson and D. L. Vaux. 2001. Genome Biol. 2, REVIEWS3009.
Verhagen, A. M, and D. L. Vaux. 2002. Apoptosis. 7: 163-6.
Verhagen, A. M, et al. 2002. J Biol. Chem. 277: 445-54.
Wang, S, and W. S. El-Deiry. 2003. Oncogene. 22: 8628-33.
Weiner, A. J., et al. 1992. Proc. Natl. Acad. Sci., USA, 89: 3468-3472.
Yu, C. L, and M. H. Tsai. 2001. Cancer Lett. 166: 173-84.
Zhang, X. D, et al. 1999. Cancer Res. 59, 2747-53.

What is claimed is:

1. A method of manufacturing a stellate cell death factor comrising the steps of (a) producing conditioned media from an immortalized hepatocyte, wherein conditioned media is culture medium used to maintain transfected primary human hepatocytes ("TPH") stably transfected with hepatitis C virus core gene or primary human hepatocytes immortalized by Simian Virus 40 T antigen ("THLE") stably transfected with hepatitis C virus core gene, (b) applying the conditioned media to at least one column, and (c) collecting fractions containing a stellate cell death factor wherein the stellate cell death factor (i) is capable of activating caspase 7 in a liver stellate cell, (ii) is associated with an approxmately 80 kD protein as determination by sodium dodecyl sulfate electrophoresis, (iii) is inactivated at 56 degrees C., and (iv) is capable of binding to albumin.

2. The method according to claim 1 wherein applying the conditioned media to at least one column comprises the steps of applying the conditioned media to an anion exchange column, collecting a flow-through from the anion exchange column, applying the flow-through to a first cation exchange column, eluting a first fraction from the first cation exchange column with a buffer having approximately 0.5M NaCl, applying the first fraction to a second cation exchange column, and eluting a second fraction containing the stellate cell death factor using an increasing gradient of NaCl.

3. A method of manufacturing a stellate death factor comprising the steps of (a) maintaining ap immortalized hepatocyte in culture, (b) collecting culture media from said culture, (c) applying said culture media to an anion exchange column and, (d) collecting the flow-through from said column wherein said flow-through contains said stellate death factor, wherein the siellate cell death factor (i) is capable of activating caspase 7 in a liver stellate cell, (ii) is. associated with an approximately 80 kD protein as determination by sodium dodecyl sulfate electrophoresis, (iii) is inactivated at 56 degrees C., (iv) is capable of binding to albumin and (v) is capable of pro-apoptotic activity in a liver stellate cell.

4. A method of manufacturing a stellate death factor as in claim 3 further comprising the step of applying said flow-through to a cation exchange column and eluting said cation exchange column with a buffer comprising approximately 0.5M or greater NaCl wherein said eluate contains said stellate death factor.

5. A method of manufacturing a stellate cell death factor as in claim 4 wherein said cation exchange column comprises a first cation exchange column and said method of manufacture further comprising a step of applying said eluate to a second cation exchange column and eluting said second cation exchange column with a gradient of 0 to 0.5M NaCl wherein said second cation exchange column eluate contains said steliate death factor.

* * * * *

SEQUENCE LISTING

```
<160> NUMBER OF SEQ ID NOS: 15

<210> SEQ ID NO 1
<211> LENGTH: 10
<212> TYPE: PRT
<213> ORGANISM: Bos taurus

<400> SEQUENCE: 1

Ile Pro Leu Asp Pro Val Ala Gly Tyr Lys
1               5                   10

<210> SEQ ID NO 2
<211> LENGTH: 10
<212> TYPE: PRT
<213> ORGANISM: Homo sapiens

<400> SEQUENCE: 2

Ala Pro His Gly Pro Gly Leu Ile Tyr Arg
1               5                   10

<210> SEQ ID NO 3
<211> LENGTH: 10
```

```
<212> TYPE: PRT
<213> ORGANISM: Mus musculus

<400> SEQUENCE: 3

Ala Pro Gln Gly Thr Gly Leu Gly Phe Arg
1               5                   10

<210> SEQ ID NO 4
<211> LENGTH: 10
<212> TYPE: PRT
<213> ORGANISM: Rattus norvegicus

<400> SEQUENCE: 4

Ala Pro Gln Gly Ala Gly Leu Gly Phe Arg
1               5                   10

<210> SEQ ID NO 5
<211> LENGTH: 359
<212> TYPE: PRT
<213> ORGANISM: Bos taurus

<400> SEQUENCE: 5

Met Lys Ser Phe Val Leu Leu Phe Cys Leu Ala Gln Leu Trp Gly Cys
1               5                   10                  15

His Ser Ile Pro Leu Asp Pro Val Ala Gly Tyr Lys Glu Pro Ala Cys
            20                  25                  30

Asp Asp Pro Asp Thr Glu Gln Ala Ala Leu Ala Val Asp Tyr Ile
        35                  40                  45

Asn Lys His Leu Pro Arg Gly Tyr Lys His Thr Leu Asn Gln Ile Asp
    50                  55                  60

Ser Val Lys Val Trp Pro Arg Pro Thr Gly Glu Val Tyr Asp Ile
65              70                  75                  80

Glu Ile Asp Thr Leu Glu Thr Thr Cys His Val Leu Asp Pro Thr Pro
                85                  90                  95

Leu Ala Asn Cys Ser Val Arg Gln Gln Thr Gln His Ala Val Glu Gly
            100                 105                 110

Asp Cys Asp Ile His Val Leu Lys Gln Asp Gly Gln Phe Ser Val Leu
        115                 120                 125

Phe Thr Lys Cys Asp Ser Ser Pro Asp Ser Ala Glu Asp Val Arg Lys
130                 135                 140

Leu Cys Pro Asp Cys Pro Leu Leu Ala Pro Leu Asn Asp Ser Arg Val
145                 150                 155                 160

Val His Ala Val Glu Val Ala Leu Ala Thr Phe Asn Ala Glu Ser Asn
                165                 170                 175

Gly Ser Tyr Leu Gln Leu Val Glu Ile Ser Arg Ala Gln Phe Val Pro
            180                 185                 190

Leu Pro Val Ser Val Ser Val Glu Phe Ala Val Ala Ala Thr Asp Cys
        195                 200                 205

Ile Ala Lys Glu Val Val Asp Pro Thr Lys Cys Asn Leu Leu Ala Glu
    210                 215                 220

Lys Gln Tyr Gly Phe Cys Lys Gly Ser Val Ile Gln Lys Ala Leu Gly
225                 230                 235                 240

Gly Glu Asp Val Arg Val Thr Cys Thr Leu Phe Gln Thr Gln Pro Val
                245                 250                 255

Ile Pro Gln Pro Gln Pro Asp Gly Ala Glu Ala Glu Ala Pro Ser Ala
            260                 265                 270

Val Pro Asp Ala Ala Gly Pro Thr Pro Ser Ala Ala Gly Pro Pro Val
```

-continued

```
                275                 280                 285
Ala Ser Val Val Gly Pro Ser Val Ala Val Pro Leu Pro Leu
        290                 295                 300

His Arg Ala His Tyr Asp Leu Arg His Thr Phe Ser Gly Val Ala Ser
305                 310                 315                 320

Val Glu Ser Ser Gly Glu Ala Phe His Val Gly Lys Thr Pro Ile
                325                 330                 335

Val Gly Gln Pro Ser Ile Pro Gly Pro Val Arg Leu Cys Pro Gly
                340                 345                 350

Arg Ile Arg Tyr Phe Lys Ile
            355

<210> SEQ ID NO 6
<211> LENGTH: 367
<212> TYPE: PRT
<213> ORGANISM: Homo sapiens

<400> SEQUENCE: 6

Met Lys Ser Leu Val Leu Leu Cys Leu Ala Gln Leu Trp Gly Cys
1               5                   10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
                35                  40                  45

Asn Gln Asn Leu Pro Trp Gly Tyr Lys His Thr Leu Asn Gln Ile Asp
        50                  55                  60

Glu Val Lys Val Trp Pro Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
                100                 105                 110

Asp Cys Asp Phe Gln Leu Leu Lys Leu Asp Gly Lys Phe Ser Val Val
            115                 120                 125

Tyr Ala Lys Cys Asp Ser Ser Pro Asp Ser Ala Glu Asp Val Arg Lys
        130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285
```

```
Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
        355                 360                 365

<210> SEQ ID NO 7
<211> LENGTH: 345
<212> TYPE: PRT
<213> ORGANISM: Mus musculus

<400> SEQUENCE: 7

Met Lys Ser Leu Val Leu Leu Leu Cys Phe Ala Gln Leu Trp Gly Cys
1               5                   10                  15

Gln Ser Ala Pro Gln Gly Thr Gly Leu Gly Phe Arg Glu Leu Ala Cys
            20                  25                  30

Asp Asp Pro Glu Ala Glu Gln Val Ala Leu Leu Ala Val Asp Tyr Leu
        35                  40                  45

Asn Asn His Leu Leu Gln Gly Phe Lys Gln Val Leu Asn Gln Ile Asp
    50                  55                  60

Lys Val Lys Val Trp Ser Arg Arg Pro Phe Gly Val Val Tyr Glu Met
65                  70                  75                  80

Glu Val Asp Thr Leu Glu Thr Thr Cys His Ala Leu Asp Pro Thr Pro
                85                  90                  95

Leu Ala Asn Cys Ser Val Arg Gln Leu Thr Glu His Ala Val Glu Gly
            100                 105                 110

Asp Cys Asp Phe His Ile Leu Lys Gln Asp Gly Gln Phe Arg Val Met
        115                 120                 125

His Thr Gln Cys His Ser Thr Pro Asp Ser Ala Glu Asp Val Arg Lys
    130                 135                 140

Leu Cys Pro Arg Cys Pro Leu Leu Thr Pro Phe Asn Asp Thr Asn Val
145                 150                 155                 160

Val His Thr Val Asn Thr Ala Leu Ala Ala Phe Asn Thr Gln Asn Asn
                165                 170                 175

Gly Thr Tyr Phe Lys Leu Val Glu Ile Ser Arg Ala Gln Asn Val Pro
            180                 185                 190

Leu Pro Val Ser Thr Leu Val Glu Phe Val Ile Ala Ala Thr Asp Cys
        195                 200                 205

Thr Ala Lys Glu Val Thr Asp Pro Ala Lys Cys Asn Leu Leu Ala Glu
    210                 215                 220

Lys Gln His Gly Phe Cys Lys Ala Asn Leu Met His Asn Leu Gly Gly
225                 230                 235                 240

Glu Glu Val Ser Val Ala Cys Lys Leu Phe Gln Thr Gln Pro Gln Pro
                245                 250                 255

Ala Asn Ala Asn Ala Val Gly Pro Val Pro Thr Ala Asn Ala Ala Leu
            260                 265                 270

Pro Ala Asp Pro Pro Ala Ser Val Val Gly Pro Val Val Val Pro
        275                 280                 285

Arg Gly Leu Ser Asp His Arg Thr Tyr His Asp Leu Arg His Ala Phe
    290                 295                 300
```

```
Ser Pro Val Ala Ser Val Glu Ser Ala Ser Gly Glu Thr Leu His Ser
305                 310                 315                 320

Pro Lys Val Gly Gln Pro Gly Ala Ala Gly Pro Val Ser Pro Met Cys
                325                 330                 335

Pro Gly Arg Ile Arg His Phe Lys Ile
                340                 345

<210> SEQ ID NO 8
<211> LENGTH: 352
<212> TYPE: PRT
<213> ORGANISM: Rattus norvegicus

<400> SEQUENCE: 8

Met Lys Ser Leu Val Leu Leu Cys Phe Ala Gln Leu Trp Ser Cys
1               5                   10                  15

Gln Ser Ala Pro Gln Gly Ala Gly Leu Gly Phe Arg Glu Leu Ala Cys
                20                  25                  30

Asp Asp Pro Glu Thr Glu His Val Ala Leu Ile Ala Val His Tyr Leu
            35                  40                  45

Asn Lys His Leu Leu Gln Gly Phe Arg Gln Ile Leu Asn Gln Ile Asp
    50                  55                  60

Lys Val Lys Val Trp Ser Arg Arg Pro Phe Gly Gln Val Tyr Glu Leu
65                  70                  75                  80

Glu Ile Asp Thr Leu Glu Thr Thr Cys His Ala Leu Asp Pro Thr Pro
                85                  90                  95

Leu Ala Asn Cys Ser Val Arg Gln Gln Ala Glu His Ala Val Glu Gly
            100                 105                 110

Asp Cys Asp Phe His Ile Leu Lys Gln Asp Gly Gln Phe Arg Val Leu
        115                 120                 125

His Ala Gln Cys His Ser Thr Pro Asp Ser Ala Glu Asp Val Arg Lys
    130                 135                 140

Phe Cys Pro Arg Cys Pro Ile Leu Ile Arg Phe Asn Asp Thr Asn Val
145                 150                 155                 160

Val His Thr Val Lys Thr Ala Leu Ala Ala Phe Asn Ala Gln Asn Asn
                165                 170                 175

Gly Thr Tyr Phe Lys Leu Val Glu Ile Ser Arg Ala Gln Asn Val Pro
            180                 185                 190

Phe Pro Val Ser Thr Leu Val Glu Phe Val Ile Ala Ala Thr Asp Cys
        195                 200                 205

Thr Gly Gln Glu Val Thr Asp Pro Ala Lys Cys Asn Leu Leu Ala Glu
    210                 215                 220

Lys Gln Tyr Gly Phe Cys Lys Ala Thr Leu Ile His Arg Leu Gly Gly
225                 230                 235                 240

Glu Glu Val Ser Val Ala Cys Lys Leu Phe Gln Thr Gln Pro Gln Pro
                245                 250                 255

Ala Asn Ala Asn Pro Ala Gly Pro Ala Pro Thr Val Gly Gln Ala Ala
            260                 265                 270

Pro Val Ala Pro Pro Ala Gly Pro Pro Glu Ser Val Val Gly Pro
        275                 280                 285

Val Ala Val Pro Leu Gly Leu Pro Asp His Arg Thr His His Asp Leu
    290                 295                 300

Arg His Ala Phe Ser Pro Val Ala Ser Val Glu Ser Ala Ser Gly Glu
305                 310                 315                 320

Val Leu His Ser Pro Lys Val Gly Gln Pro Gly Asp Ala Gly Ala Ala
```

```
                    325                 330                 335
Gly Pro Val Ala Pro Leu Cys Pro Gly Arg Val Arg Tyr Phe Lys Ile
            340                 345                 350
```

<210> SEQ ID NO 9
<211> LENGTH: 8
<212> TYPE: PRT
<213> ORGANISM: Bos taurus

<400> SEQUENCE: 9

```
Asp Thr His Lys Ser Glu Ile Ala
1               5
```

<210> SEQ ID NO 10
<211> LENGTH: 21
<212> TYPE: DNA
<213> ORGANISM: mammalian

<400> SEQUENCE: 10
caccttagtg cagcgcttct a                                          21

<210> SEQ ID NO 11
<211> LENGTH: 24
<212> TYPE: DNA
<213> ORGANISM: mammalian

<400> SEQUENCE: 11
aggtctctca gcaccaggtc tagg                                       24

<210> SEQ ID NO 12
<211> LENGTH: 21
<212> TYPE: DNA
<213> ORGANISM: mammalian

<400> SEQUENCE: 12
aacgcgtctg ccccattcaa c                                          21

<210> SEQ ID NO 13
<211> LENGTH: 22
<212> TYPE: DNA
<213> ORGANISM: mammalian

<400> SEQUENCE: 13
gacggccaca ctgcacaaga ga                                         22

<210> SEQ ID NO 14
<211> LENGTH: 21
<212> TYPE: DNA
<213> ORGANISM: mammalian

<400> SEQUENCE: 14
gaagatgttc ttggcagctc t                                          21

<210> SEQ ID NO 15
<211> LENGTH: 20
<212> TYPE: DNA
<213> ORGANISM: mammalian

<400> SEQUENCE: 15
gatcccaggg taaagccaat                                            20